(12) United States Patent
Fischer et al.

(10) Patent No.: US 9,458,380 B2
(45) Date of Patent: Oct. 4, 2016

(54) 5H-FURAN-2-ONE DERIVATIVES FOR STABILIZATION OF ORGANIC MATERIAL

(75) Inventors: Walter Fischer, Reinach (CH); Abdel-Ilah Basbas, Basel (CH); Kai-Uwe Schoning, Oberwil (CH); Cinzia Tartarini, Basel (CH); Werner Holzl, Eschentzwiller (FR); Bruno Rotzinger, Delemont (CH)

(73) Assignee: BASF SE, Ludwigshafen (DE)

( * ) Notice: Subject to any disclaimer, the term of this patent is extended or adjusted under 35 U.S.C. 154(b) by 82 days.

(21) Appl. No.: 14/114,538

(22) PCT Filed: Apr. 25, 2012

(86) PCT No.: PCT/IB2012/052064
§ 371 (c)(1),
(2), (4) Date: Oct. 29, 2013

(87) PCT Pub. No.: WO2012/150527
PCT Pub. Date: Nov. 8, 2012

(65) Prior Publication Data
US 2014/0058021 A1    Feb. 27, 2014

Related U.S. Application Data

(60) Provisional application No. 61/481,272, filed on May 2, 2011.

(30) Foreign Application Priority Data

May 2, 2011 (EP) ..................... 11164465

(51) Int. Cl.
*C09K 15/06* (2006.01)
*C08K 5/1535* (2006.01)
*C08K 5/52* (2006.01)
*C07D 307/58* (2006.01)
(Continued)

(52) U.S. Cl.
CPC ............. *C09K 15/06* (2013.01); *C07D 307/58* (2013.01); *C07D 307/64* (2013.01); *C07D 405/12* (2013.01); *C08K 5/1535* (2013.01); *C08K 5/52* (2013.01)

(58) Field of Classification Search
CPC  C07D 307/58; C07D 307/64; C07D 405/12; C09K 15/06; C08K 5/1535; C08K 5/52
USPC ........... 524/111; 544/152; 546/214; 549/295, 549/313, 320, 321, 322, 679
See application file for complete search history.

(56) References Cited

U.S. PATENT DOCUMENTS 3,644,573 A    2/1972 Barkey et al.
4,603,205 A    7/1986 Neumann et al.
(Continued)

FOREIGN PATENT DOCUMENTS

CN    1914151 A    2/2007
EP    1291384 A1    3/2003
(Continued)

OTHER PUBLICATIONS

KR 1020080065561 A (2008), machine translation, KIPO Korean Intellectual Property Information Service (KIPRIS).*
Alan R. Katritzky et al., Journal Organic Chemistry, 1997, 62, pp. 715-720.
Mcrae, et al., Journal of the American Chemical Society, vol. 52, 1930, pp. 3377-3382.
Karl Gewald, Chemische Berichte, Verlag Chemie GMBH. vol. 99, No. 3, Jan. 1, 1966, pp. 1002-1007.
English language translation of CN 1 914 151 Feb. 14, 2007.
International Search Report Sep. 13, 2012.
European Search Report Oct. 31, 2011.

*Primary Examiner* — Susannah Chung
*Assistant Examiner* — Josephine Chang
(74) *Attorney, Agent, or Firm* — Marshall, Gerstein & Borun LLP

(57) ABSTRACT

A composition, which comprises a) an organic material susceptible to oxidative, thermal or light-induced degradation; and b) a compound of formula I (Formula I) (I) wherein $R_1$, $R_2$, $R_3$, $R_4$, $R_5$, $R_6$, $R_7$, $R_8$, $R_9$ and $R_{10}$ are independently from each other H, $C_1$-$C_8$-alkyl, $C_4$-$C_8$-cycloalkyl, phenyl, $C_1$-$C_4$-alkoxy or halogen; n is 1, 2, 3, or 4; and when n is 1 A is —C(=O)-OR'$_1$, —C(=O)-N(R'$_2$)(R'$_3$), —CN, phenyl, which is unsubstituted or substituted by one or more $C_1$-$C_8$-alkyl, $C_4$-$C_8$-alkoxy, $C_5$-$C_7$-cycloalkyl or halogen, —H or —SO$_2$-phenyl; when n is 2 A is —C(=O)-O—Z$_1$—O—C (=O)-, —C(=O)-N(R"$_1$)—Z$_2$—N(R"$_2$)—C(=O)- or piperazine-N,N'-biscarbonyl.

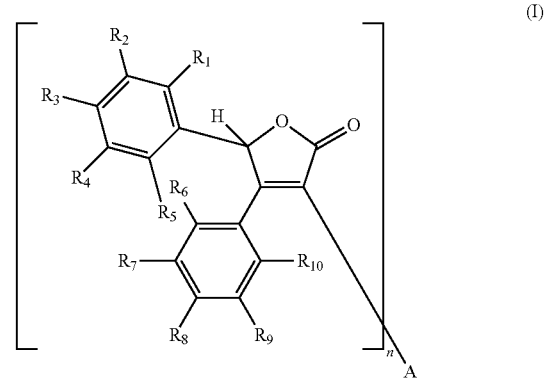

8 Claims, No Drawings

(51) Int. Cl.
*C07D 307/64* (2006.01)
*C07D 405/12* (2006.01)

(56) References Cited

U.S. PATENT DOCUMENTS

| | | |
|---|---|---|
| 4,703,072 A | 10/1987 | Helwig et al. |
| 5,883,165 A | 3/1999 | Kroehnke et al. |
| 6,881,774 B2 | 4/2005 | Schrinner et al. |
| 7,468,410 B2 * | 12/2008 | Chafin .................. C07F 9/145 524/128 |
| 2003/0083405 A1 | 5/2003 | Wang et al. |
| 2012/0230925 A1 | 9/2012 | Winkler et al. |

FOREIGN PATENT DOCUMENTS

| | | |
|---|---|---|
| GB | 2281910 A | 3/1995 |
| JP | 2006221973 A | 8/2006 |
| KR | 20080065561 A | 7/2008 |
| RU | 2286361 C2 | 10/2006 |

\* cited by examiner

5H-FURAN-2-ONE DERIVATIVES FOR STABILIZATION OF ORGANIC MATERIAL

Organic materials are susceptible to degradation, which can be induced by heat, light and/or oxidation. For reducing such degradation, numerous solutions in regard to an incorporation or addition of a stabilizer are proposed.

There is still a need for further technical solutions towards stabilisation of organic material against the detrimental impact of heat, light and/or oxidation.

US-A-2003/0083405 discloses inter alia 5H-dihydrofuran-2-one derivatives as antioxidants for stabilization of a polymer.

It has now been found that a specific group of 5H-dihydro-furan-2-one derivatives are suitable for stabilization of organic material against degradation by heat, light and/or oxidation.

The present invention relates to a composition, which comprises
a) an organic material susceptible to oxidative, thermal or light-induced degradation; and
b) a compound of formula I

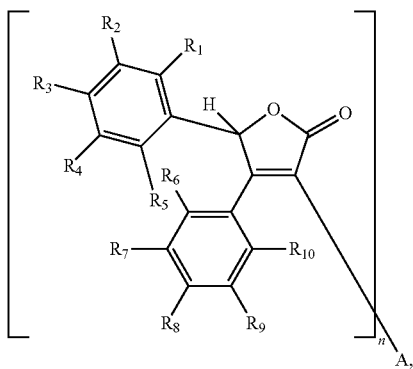

wherein
when n is 1
A is —C(=O)—OR'$_1$, —C(=O)—N(R'$_2$)(R'$_3$), —CN, phenyl, which is unsubstituted or substituted by one or more $C_1$-$C_8$-alkyl, $C_1$-$C_4$-alkoxy, $C_5$-$C_7$-cycloalkyl or halogen, —H or —SO$_2$-phenyl;
when n is 2
A is —C(=O)—O—Z$_1$—O—C(=O)—, —C(=O)—N(R"$_1$)—Z$_2$—N(R"$_2$)—C(=O)— or piperazine-N,N'-bis-carbonyl;
when n is 3
A is $C_3$-$C_{12}$-alkane-tri-(oxycarbonyl), 3-ethyl-3-azapentane-1,5,2'-tri-(oxycarbonyl), 1,4,7-triazaheptane-1,4,7-tricarbonyl, 1,4,8-triazaoctane-1,4,8-tricarbonyl or 1,5,9-triazanonane-1,5,9-tricarbonyl;
when n is 4
A is $C_4$-$C_{16}$-alkane-tetra-(oxycarbonyl), 1,4,7,10-tetraazadecane-1,4,7,10-tetracarbonyl, 1,4,8,11-tetraazaundecane-1,4,8,11-tetracarbonyl or 1,5,8,12-tetraazadodecane-1,5,8,12-tetracarbonyl;
n is 1, 2, 3 or 4;
$R_1$, $R_2$, $R_3$, $R_4$, $R_5$, $R_6$, $R_7$, $R_8$, $R_9$ and $R_{10}$ are independently from each other H, $C_1$-$C_8$-alkyl, $C_4$-$C_8$-cycloalkyl, phenyl, $C_1$-$C_4$-alkoxy or halogen;
R'$_1$ is H, $C_1$-$C_{22}$-alkyl, $C_2$-$C_{18}$-alkenyl, $C_3$-$C_{12}$-alkine-yl, $C_4$-$C_8$-cycloalkyl, which is unsubstituted or substituted by one to three $C_1$-$C_4$-alkyl, $C_4$-$C_8$-cycloalkyl-$C_1$-$C_4$-alkyl, bicyclic or tricyclic $C_5$-$C_{20}$-alkyl, $C_6$-$C_{14}$-aryl-$C_1$-$C_4$-alkyl, $C_2$-$C_{12}$-alkyl, which is substituted by one or more hydroxyl groups, $C_4$-$C_{12}$-alkyl, which is interrupted by one or more oxygen atoms, $C_4$-$C_{18}$-alkyl, which is interrupted by one sulfur atom, 2,2,6,6-tetramethylpiperidine-4-yl, 1-($C_1$-$C_8$-alkyl)-2,2,6,6-tetramethylpiperidine-4-yl or 1-($C_1$-$C_8$-alkoxy)-2,2,6,6-tetramethylpiperidine-4-yl;
R'$_2$ and R'$_3$ are independently from each other H, $C_1$-$C_{22}$-alkyl, $C_2$-$C_{18}$-alkenyl, $C_4$-$C_8$-cycloalkyl, which is unsubstituted or substituted by one to three $C_1$-$C_4$-alkyl, $C_4$-$C_8$-cycloalkyl-$C_1$-$C_4$-alkyl, $C_6$-$C_{14}$-aryl-$C_1$-$C_4$-alkyl, $C_2$-$C_6$-alkyl, which is substituted by a hydroxyl group, $C_6$-$C_{10}$-aryl, 2,2,6,6-tetramethylpiperidine-4-yl, 1-($C_1$-$C_8$-alkyl)-2,2,6,6-tetramethylpiperidine-4-yl or 1-($C_1$-$C_8$-alkoxy)-2,2,6,6-tetramethylpiperidine-4-yl, or R'$_2$ and R'$_3$ form together with the nitrogen atom to which they are attached a 5-, 6- or 7-membered saturated heterocycle;
R"$_1$ and R"$_2$ are independently from each other H, $C_1$-$C_{22}$-alkyl, $C_2$-$C_{18}$-alkenyl, $C_4$-$C_8$-cycloalkyl, which is unsubstituted or substituted by one to three $C_1$-$C_4$-alkyl, $C_4$-$C_8$-cycloalkyl-$C_1$-$C_4$-alkyl, $C_6$-$C_{14}$-aryl-$C_1$-$C_4$-alkyl;
$Z_1$ is $C_2$-$C_{12}$-alkylene, $C_4$-$C_8$-cycloalkylene, $C_4$-$C_8$-cycloalkane-bis-($C_1$-$C_4$-alkylene), $C_6$-$C_{14}$-arene-bis-($C_1$-$C_4$-alkylene), $C_3$-$C_6$-alkylene, which is substituted by one or more hydroxyl groups, $C_4$-$C_{12}$-alkylene, which is interrupted by one or more oxygen atoms, hexahydro-furo[3,2-b]furane-3,6-diyl, $C_4$-$C_8$-alkylene, which is interrupted by a sulfur atom, 3-($C_1$-$C_8$-alkyl)-3-azapentane-1,5-diyl, 4-($C_1$-$C_8$-alkyl)-4-azaheptane-1,7-diyl or 1-ethyl-2,2,6,6-tetramethylpiperidine-4,2'-diyl; and
$Z_2$ is $C_2$-$C_{12}$-alkylene, $C_4$-$C_8$-cycloalkylene, $C_6$-$C_{14}$-arylene, $C_4$-$C_8$-cycloalkane-bis($C_1$-$C_4$-alkylene), $C_6$-$C_{14}$-arene-bis-($C_1$-$C_4$-alkylene), $C_4$-$C_{12}$-alkylene, which is interrupted by one or more oxygen atoms, 3-($C_1$-$C_8$-alkyl)-3-azapentane-1,5-diyl or 4-($C_1$-$C_8$-alkyl)-4-azaheptane-1,7-diyl.

A compound of formula I possess at least one asymmetric carbon atom, i.e. the carbon atom at the 5-position of the furan-2-one ring, which results in enantiomers. The invention relates to any one of these enantiomers or mixtures thereof. Several combinations of substituents at formula I lead to the presence of at least two asymmetric carbon atoms, which results in diastereomers. The invention relates to any one of these diastereomers or mixtures thereof.

$C_1$-$C_{22}$-alkyl is linear or branched and for example methyl, ethyl, n-propyl, 1-methyl-ethyl, n-butyl, 1-methyl-propyl, 2-methyl-propyl, 1,1-dimethyl-ethyl, n-pentyl, 1-methyl-butyl, 3-methyl-butyl, n-hexyl, 1-methyl-pentyl, 2-methyl-pentyl, 4-methyl-pentyl, 2-ethyl-butyl, n-heptyl, 1-methyl-hexyl, n-octyl, 1-methyl-heptyl, 2-ethyl-hexyl, 5,5-dimethyl-hexyl, 1,1,3,3-tetramethyl-butyl, n-nonyl, 2-ethyl-heptyl, n-decyl, undecyl, n-dodecyl, tridecyl, tetradecyl, pentadecyl, n-hexadecyl or n-octadecyl. Preferred is $C_1$-$C_{18}$-alkyl, in particular $C_1$-$C_{12}$-alkyl, especially $C_1$-$C_8$-alkyl, very especially $C_1$-$C_4$-alkyl.

$C_2$-$C_{18}$-alkenyl is linear or branched and for example vinyl, allyl, Z- or E-but-2-ene-yl, Z- or E-but-3-ene-yl, Z- or E-pent-2-ene-yl, pent-4-ene-yl, Z- or E-2-methyl-but-2-ene-yl, Z- or E-3-methyl-but-3-ene-yl, Z- or E-hex-1-ene-yl, Z- or E-hexadec-9-ene-yl or Z- or E-octadec-9-ene-yl.

$C_3$-$C_{12}$-alkine-yl is for example propargyl, but-2-ine-yl or undec-11-ine-yl.

$C_4$-$C_8$-cycloalkyl is for example cyclobutyl, cyclopentyl, cyclohexyl, cycloheptyl or cyclooctyl. Preferred is $C_5$-$C_7$-cycloalkyl, in particular cyclohexyl.

$C_4$-$C_8$-cycloalkyl, which is substituted by one to three $C_1$-$C_4$-alkyl, is for example 3,4-dimethyl-cyclopentyl, 4-methyl-cyclohexyl, 2-methyl-cyclohexyl, 3,5-dimethyl-cyclohexyl or 4-(1-methyl-ethyl)-cyclohexyl or 5-methyl-2-(1-methyl-ethyl)-cyclohexyl.

$C_6$-$C_{10}$-aryl is for example phenyl, 2-methyl-phenyl, 3-methyl-phenyl, 4-methyl-phenyl, 2,4-dimethyl-phenyl, 4-(1,1-dimethylethyl)-phenyl, biphenyl-4-yl, napthalen-1-yl or napthalen-2-yl. Preferred is phenyl.

Bicyclic or tricyclic $C_5$-$C_{20}$-alkyl is for example 2-methyl-bicyclo[2.2.1]heptane-1'-yl, 1,7,7-trimethylbicyclo[2.2.1]heptane-2-yl, adamantane-yl, 1-methyl-adamantane-1'-yl or 1,3-dimethyl-adamantane-1'-yl.

$C_4$-$C_8$-cycloalkyl-$C_1$-$C_4$-alkyl is for example 2-(cyclopentyl)-ethyl, cyclohexyl-methyl, 2-(cyclohexyl)-ethyl, 2-(cyclohexyl)-1-methyl-ethyl or (cycloheptyl)-methyl.

$C_6$-$C_{14}$-aryl-$C_1$-$C_4$-alkyl is for example benzyl, 4-methyl-benzyl, 2-phenyl-ethyl, 3,5-dimethylbenzyl, 1-phenyl-1,1-dimethyl-methyl, 3-phenyl-propyl, 3-phenyl-2-methyl-propyl, 3,5-di-tert-butyl-benzyl or biphenyl-4-yl-methyl.

$C_2$-$C_{12}$-alkyl, which is substituted by one or more hydroxyl groups, is for example 2-hydroxy-ethyl, 3-hydroxy-propyl, 2-hydroxy-2-methyl-ethyl, 2,2-dimethyl-3-hydroxy-propyl, 4-hydroxy-butyl, 6-hydroxy-hexyl, 2,3-dihydroxy-propyl, 2-hydroxy-butyl, 2-hydroxy-hexyl, 1,3-dihydroxy-propane-2-yl, 2,3,4,5-tetrahydroxy-pentyl or 2,3,4,5,6-pentahydroxy-hexyl. Preferred is $C_2$-$C_8$-alkyl, which is substituted by one hydroxyl group. Preferred in particular is 2-hydroxy-ethyl or 2-hydroxy-2-methyl-ethyl.

$C_1$-$C_8$-alkoxy is for example methoxy, ethoxy, n-propoxy, 1-methyl-ethoxy, n-butoxy, 1-methyl-propoxy, 2-methyl-propoxy, 1,1-dimethyl-ethoxy, n-pentoxy, 1-methyl-butoxy, 2-methyl-butoxy, 3-methyl-butoxy, n-hexane-oxy, n-heptane-oxy, n-octane-oxy or 1-methyl-heptane-oxy. $C_1$-$C_4$-alkoxy is preferred.

Phenyl, which is unsubstituted or substituted by one or more $C_1$-$C_8$-alkyl, $C_1$-$C_4$-alkoxy, $C_5$-$C_7$-cycloalkyl or halogen, is for example phenyl, 2-methyl-phenyl, 3-methyl-phenyl, 3,5-dimethyl-phenyl, 4-methyl-phenyl, 3-(1-methyl-propyl)-phenyl, 4-(1-methyl-propyl)-phenyl, 4-(1,1-dimethyl-ethyl)-phenyl, 4-(1,1,3,3-tetramethyl-butyl)-phenyl, 4-cyclohexyl-phenyl, biphenyl-4-yl, 2-methoxy-phenyl, 3-methoxy-phenyl, 4-methoxy-phenyl, 4-ethoxy-phenyl, 2-chloro-phenyl, 3-chloro-phenyl, 4-chloro-phenyl or 4-bromo-phenyl. Preferred is phenyl, which is unsubstituted or substituted by one $C_1$-$C_8$-alkyl, $C_1$-$C_4$-alkoxy, $C_5$-$C_7$-cycloalkyl or halogen. Preferred is phenyl, which is unsubstituted.

$C_4$-$C_{12}$-alkyl, which is interrupted by one or more oxygen atoms, is for example 2-ethoxy-ethyl, 2-(2-methoxy-ethoxy)-ethyl, 2-n-butoxy-ethyl, 2-[2-(2-methoxy-ethoxy)-ethoxy]-ethyl, 2-[2-[2-(2-methoxy-ethoxy)-ethoxy]-ethoxy]-ethyl, 2-(2-methoxy-1-methyl-ethoxy)-1-methyl-ethyl, 3-(n-propoxy)-propyl, 2-(2-hydroxy-ethoxy)-ethyl, 2-[2-[2-(2-hydroxy-ethoxy)-ethoxy]-ethoxy]-ethyl or 2-[2-(2-hydroxy-2-methyl-ethoxy)-2-methyl-ethoxy]-2-methyl-ethyl.

$C_4$-$C_{16}$-alkyl, which is interrupted by one sulfur atom, is for example 3-thiaundecyl or 3-thiapentadecyl.

Halogen is for example a chlorine atom, a bromine atom or iodine atom. Preferred is a chlorine atom.

$C_2$-$C_{12}$-alkylene is for example ethylene, 1-methyl-ethane-1,2-diyl, n-propylene, n-butylene, 2-methyl-butane-1,4-diyl, hexamethylene or decane-1,10-diyl.

$C_4$-$C_8$-cycloalkylene is for example cyclopentane-1,2-diyl, cyclopentane-1,3-diyl, cyclohexane-1,4-diyl, cyclohexane-1,2-diyl, cyclooctane-1,2-diyl or cycloheptane-1,3-diyl.

$C_6$-$C_{14}$-arylene is for example 1,3-phenylene, 1,4-phenylene, 2,3-dimethyl-benzene-1,4-diyl, biphenyl-4,4'-diyl, naphtalene-2,6-diyl or naphthalene-1,4-diyl.

$C_4$-$C_8$-cycloalkane-bis-($C_1$-$C_4$-alkylene) is for example cyclopentane-1,3-bismethylene, cyclohexane-1,4-bismethylene, cyclohexane-1,3-bismethylene, cyclohexane-1,4-bisethylene or cyclohexane-1,4-bis(1-methyl-ethane-1,2-diyl).

$C_6$-$C_{14}$-arene-bis-($C_1$-$C_4$-alkylene) is for example benzene-1,3-bismethylene, benzene-1,4-bismethylene, napthaline-1,4-bismethylene, napthaline-2,6-bismethylene, 5-methyl-benzene-1,3-bismethylene, 5-tert-butyl-benzene-1,3-bismethylene, benzene-1,4-bisethylene, benzene-1,4-bis-(1-methyl-ethan-1,2-diyl) or biphenyl-4,4'-bismethylene.

$C_3$-$C_6$-alkylene, which is substituted by one or more hydroxyl groups, is for example 2-hydroxy-propane-1,3-diyl, 1-hydroxymethyl-ethane-1,2-diyl, 2,3,4-trihydroxy-pentane-1,5-diyl, 2,3,4-trihydroxyhexane-1,6-diyl or 2,3,4,5-tetrahydroxy-hexane-1,6-diyl.

$C_4$-$C_{12}$-alkylene, which is interrupted by one or more oxygen atoms, is for example 2-ethoxyethane-1,2'-diyl, —($CH_2CH_2$—O)$_2$—$CH_2CH_2$—, —($CH_2CH_2$—O)$_3$—$CH_2CH_2$—, —$CH(CH_3)CH_2$—O—$CH(CH_3)CH_2$—, —[$CH(CH_3)CH_2$—O]$_2$—$CH(CH_3)CH_2$—, —$CH_2CH_2CH_2CH_2$—O—$CH_2CH_2CH_2CH_2$— or —($CH_2CH_2CH_2CH_2$—O)$_2$—$CH_2CH_2CH_2CH_2$—.

$C_4$-$C_8$-alkylene, which is interrupted by one sulfur atom, is for example —$CH_2CH_2$—S—$CH_2CH_2$—, —$CH_2CH_2CH_2$—S—$CH_2CH_2CH_2$— or —$CH(CH_3)CH_2$—S—$CH_2$—$CH(CH_3)$—.

3-($C_1$-$C_8$-alkyl)-3-azapentane-1,5-diyl is for example $CH_2CH_2$—N($CH_3$)—$CH_2CH_2$— or —$CH_2CH_2$—N($CH_2$—C($CH_3$)$_2$—$CH_2$—$CH_3$)—$CH_2CH_2$—.

4-($C_1$-$C_8$-alkyl)-4-azaheptane-1,7-diyl is for example $CH_2CH_2CH_2$—N($CH_3$)—$CH_2CH_2CH_2$— or —$CH_2CH_2$—N($CH_2$—C($CH_3$)$_2$—$CH_2$—$CH_3$)—$CH_2CH_2CH_2$—.

A 5-, 6- or 7-membered saturated heterocycle is for example pyrrolidine, piperidine, azepane, morpholine or 2,6-dimethyl-morpholine.

The sign 'star' (=–*) indicates the free bonding valence of the carbon atom at the depicted radicals below.

Hexahydro-furo[3,2-b]furane-3,6-diyl is a divalent radical as depicted:

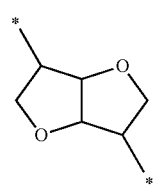

Piperazine-N,N'-biscarbonyl is a divalent radical as depicted:

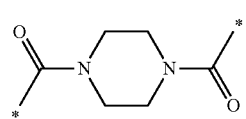

1-Ethyl-2,2,6,6-tetramethylpiperidine-4,2'-diyl is a divalent radical as depicted:

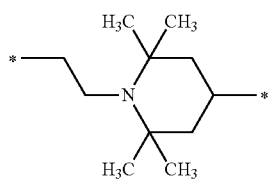

$C_3$-$C_{12}$-alkane-tri-(oxycarbonyl) is a trivalent radical and for example propane-1,2,3-tri-(oxycarbonyl) as depicted:

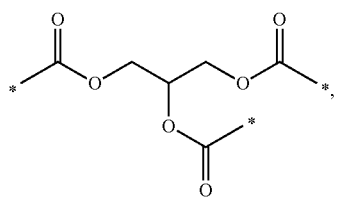

2-methyl-propane-1,2,3-tri-(oxycarbonyl) as depicted:

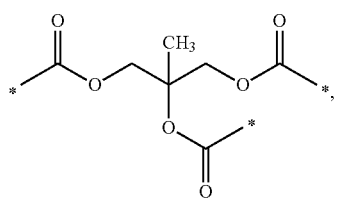 [SMILES: CC(=O)OCC(C)(COC(C)=O)OC(C)=O]

2-methyl-butane-1,2,1'-tri-(oxycarbonyl) as depicted:

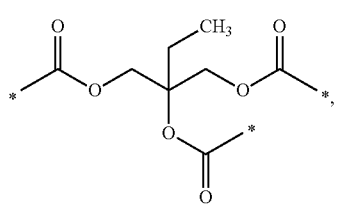 [SMILES: CCC(COC(C)=O)(COC(C)=O)OC(C)=O]

2,2-dimethyl-butane-1,1',1"-tri-(oxycarbonyl) as depicted:

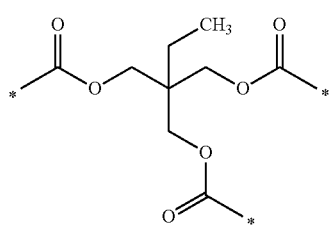 [SMILES: CCC(COC(C)=O)(COC(C)=O)COC(C)=O]

or
2,2-dimethyl-pentane-1,1',1"-tri-(oxycarbonyl) as depicted:

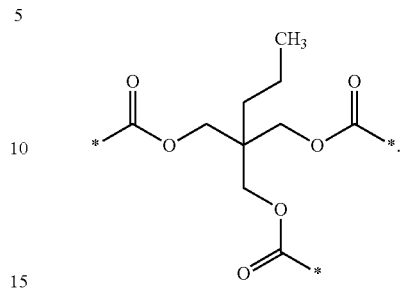

3-Ethyl-3-azapentane-1,5,2'-tri-(oxycarbonyl) is a trivalent radical as depicted:

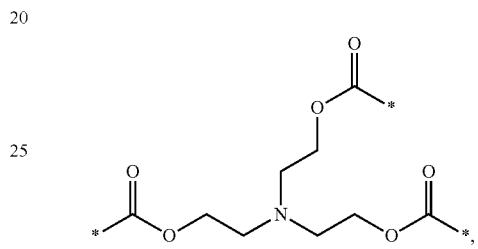

1,4,7-Triazaheptane-1,4,7-tricarbonyl is a trivalent radical as depicted:

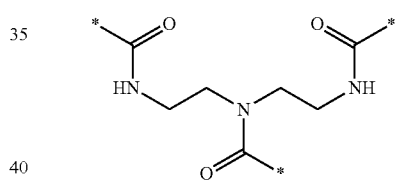

1,4,8-Triazaoctane-1,4,8-tricarbonyl is a trivalent radical as depicted:

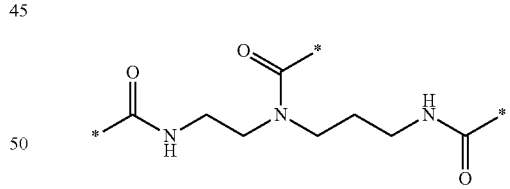

1,5,9-Triazanonane-1,5,9-tricarbonyl is a trivalent radical as depicted:

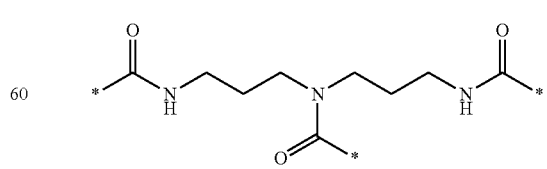

$C_4$-$C_{16}$-alkane-tetra-(oxycarbonyl) is a tetravalent radical and for example 2,2-dimethyl-propane-1,3,1',1"-tetra-(oxycarbonyl) as depicted:

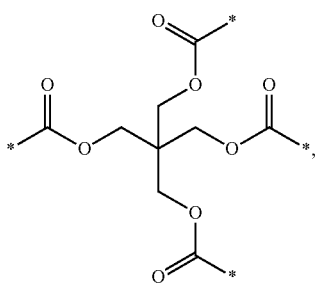

butane-1,2,3,4-tetra-(oxycarbonyl) as depicted:

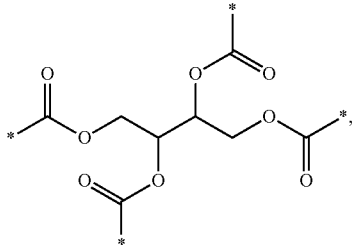

hexane-1,3,4,6-tetra-(oxycarbonyl) as depicted:

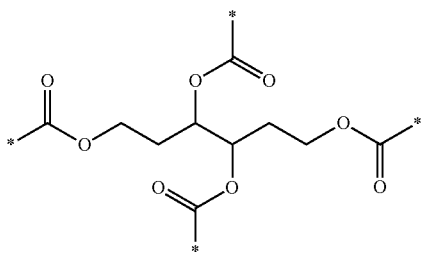 [SMILES: *C(=O)OCCC(OC(*)=O)C(CCOC(*)=O)OC(*)=O]

or
octane-1,3,6,8-tetra-(oxycarbonyl) as depicted:

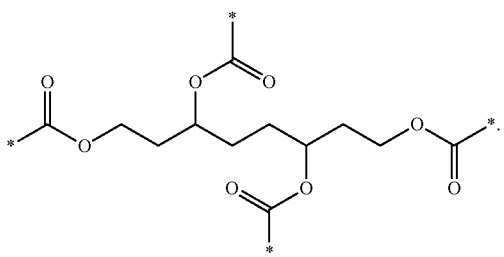

1,4,7,10-Tetraazadecane-1,4,7,10-tetracarbonyl is a tetravalent radical as depicted:

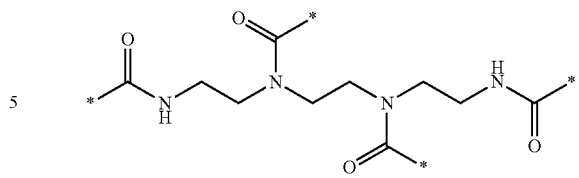

1,4,8,11-Tetraazaundecane-1,4,8,11-tetracarbonyl is a tetravalent radical as depicted:

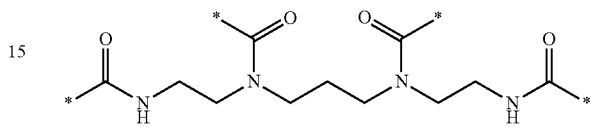

1,5,8,12-Tetraazadodecane-1,5,8,12-tetracarbonyl is a tetravalent radical as depicted:

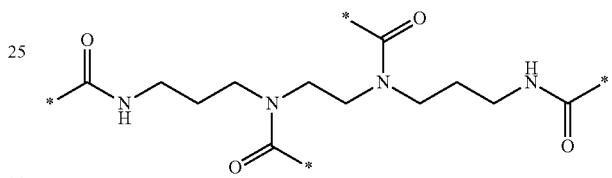

Preferred is a compound of formula I, wherein
$R_1$, $R_2$, $R_3$, $R_4$, $R_5$, $R_6$, $R_7$, $R_8$, $R_9$ and $R_{10}$ are independently from each other H, $C_1$-$C_8$-alkyl, $C_4$-$C_8$-cycloalkyl, phenyl, $C_1$-$C_4$-alkoxy or halogen, with the proviso that at least $R_1$ or $R_5$ is H and at least $R_6$ or $R_{10}$ is H.

Preferred is a compound of formula I, wherein
$R_1$, $R_2$, $R_3$, $R_4$ and $R_5$ are independently from each other H, $C_1$-$C_8$-alkyl, $C_4$-$C_8$-cycloalkyl, phenyl, $C_1$-$C_4$-alkoxy or halogen;
$R_6$ is $R_1$; $R_7$ is $R_2$; $R_8$ is $R_3$; $R_9$ is $R_4$ and $R_{10}$ is $R_5$.

Preferred is a compound of formula I, wherein
$R_1$, $R_2$, $R_3$, $R_4$ and $R_5$ are independently from each other H, $C_1$-$C_8$-alkyl, $C_4$-$C_8$-cycloalkyl, phenyl, $C_1$-$C_4$-alkoxy or halogen, with the proviso that at least $R_1$ is H;
$R_6$ is $R_1$; $R_7$ is $R_2$; $R_8$ is $R_3$; $R_9$ is $R_4$ and $R_{10}$ is $R_5$.

Preferred is a compound of formula I, wherein
$R_1$, $R_2$, $R_3$, $R_4$, $R_5$, $R_6$, $R_7$, $R_8$, $R_9$ and $R_{10}$ are independently from each other H, methyl or methoxy.

Preferred is a compound of formula I, wherein
$R_1$, $R_2$, $R_4$, $R_5$, $R_6$, $R_7$, $R_9$ and $R_{10}$ are H; and
$R_3$ and $R_8$ are independently from each other H, $C_1$-$C_8$-alkyl, $C_1$-$C_4$-cycloalkyl, phenyl, $C_1$-$C_4$-alkoxy or halogen.

Preferred is a compound of formula I, wherein
$R_1$, $R_2$, $R_4$, $R_5$, $R_6$, $R_7$, $R_9$ and $R_{10}$ are H; and
$R_3$ and $R_8$ are independently from each other H, $C_1$-$C_8$-alkyl, phenyl or $C_1$-$C_4$-alkoxy.

Preferred is a compound of formula I, wherein
$R_1$, $R_2$, $R_4$, $R_5$, $R_6$, $R_7$, $R_9$ and $R_{10}$ are H; and
$R_3$ and $R_8$ are independently from each other H, $C_1$-$C_8$-alkyl or $C_1$-$C_4$-alkoxy.

Preferred is a compound of formula I, wherein
$R_1$, $R_2$, $R_4$, $R_5$, $R_6$, $R_7$, $R_9$ and $R_{10}$ are H; and
$R_3$ and $R_8$ are independently from each other H or methoxy.

Preferred is a compound of formula I, wherein
$R_1$, $R_2$, $R_3$, $R_4$, $R_5$, $R_6$, $R_7$, $R_8$, $R_9$ and $R_{10}$ are H.

Preferred is a compound of formula I, wherein
R'$_3$ is H; and
R"$_2$ and R"$_3$ are H.
Preferred is a compound of formula I, wherein
n is 1, 2 or 3.
Preferred is a compound of formula I, wherein
n is 1 or 2.
Preferred is a compound of formula I, wherein
when n is 1
A is —C(=O)—OR'$_1$, —C(=O)—N(R'$_2$)(R'$_3$), —CN, phenyl, which is substituted by one or more C$_1$-C$_8$-alkyl, C$_1$-C$_4$-alkoxy, C$_5$-C$_7$-cycloalkyl or halogen, —H or —SO$_2$-phenyl.
Preferred is a compound of formula I, wherein
when n is 1
A is —C(=O)—OR'$_1$, —C(=O)—N(R'$_2$)(R'$_3$), —CN, —H or —SO$_2$-phenyl.
Preferred is a compound of formula I, wherein
when n is 2
A is —C(=O)—O—Z$_1$—O—C(=O)—;
when n is 3
A is C$_3$-C$_{12}$-alkane-tri-(oxycarbonyl);
when n is 4
A is C$_4$-C$_{16}$-alkane-tetra-(oxycarbonyl).
Preferred is a compound of formula I, wherein
when n is 1
A is —C(=O)—OR'$_1$, —CN, phenyl, which is unsubstituted or substituted by one or more C$_1$-C$_8$-alkyl, C$_1$-C$_4$-alkoxy, C$_5$-C$_7$-cycloalkyl or halogen, —H or —SO$_2$-phenyl;
when n is 2
A is —C(=O)—O—Z$_1$—O—C(=O)—;
when n is 3
A is C$_3$-C$_{12}$-alkane-tri-(oxycarbonyl);
when n is 4
A is C$_4$-C$_{16}$-alkane-tetra-(oxycarbonyl).
Preferred is a compound of formula I, wherein
when n is 1
A is —C(=O)—OR'$_1$, —C(=O)—N(R'$_2$)(R'$_3$), —CN, phenyl, which is unsubstituted or substituted by one or more C$_1$-C$_8$-alkyl, C$_1$-C$_4$-alkoxy, C$_5$-C$_7$-cycloalkyl or halogen, —H or —SO$_2$-phenyl;
when n is 2
A is —C(=O)—O—Z$_1$—O—C(=O)— or —C(=O)—N(R"$_1$)—Z$_2$—N(R"$_2$)—C(=O)—;
when n is 3
A is C$_3$-C$_{12}$-alkane-tri-(oxycarbonyl) or 3-ethyl-3-azapentane-1,5,2'-tri-(oxycarbonyl);
when n is 4
A is C$_4$-C$_{16}$-alkane-tetra-(oxycarbonyl);
n is 1, 2, 3 or 4;
R$_1$, R$_2$, R$_3$, R$_4$, R$_5$, R$_6$, R$_7$, R$_8$, R$_9$ and R$_{10}$ are independently from each other H, C$_1$-C$_8$-alkyl, C$_4$-C$_8$-cycloalkyl, phenyl, C$_1$-C$_4$-alkoxy or halogen;
R'$_1$ is H, C$_1$-C$_{22}$-alkyl, C$_2$-C$_{18}$-alkenyl, C$_3$-C$_{12}$-alkinyl, C$_4$-C$_8$-cycloalkyl, which is unsubstituted or substituted by one to three C$_1$-C$_4$-alkyl, C$_4$-C$_8$-cycloalkyl-C$_1$-C$_4$-alkyl, bicyclic or tricyclic C$_5$-C$_{20}$-alkyl, C$_6$-C$_{14}$-aryl-C$_1$-C$_4$-alkyl, C$_2$-C$_{12}$-alkyl, which is substituted by one or more hydroxyl groups, C$_4$-C$_{12}$-alkyl, which is interrupted by one or more oxygen atoms, C$_4$-C$_{18}$-alkyl, which is interrupted by one sulfur atom, 2,2,6,6-tetramethylpiperidine-4-yl, 1-(C$_1$-C$_8$-alkyl)-2,2,6,6-tetramethylpiperidine-4-yl or 1-(C$_1$-C$_8$-alkoxy)-2,2,6,6-tetramethylpiperidine-4-yl;
R'$_2$ and R'$_3$ are independently from each other H, C$_1$-C$_{22}$-alkyl, C$_2$-C$_{18}$-alkenyl, C$_4$-C$_8$-cycloalkyl, which is unsubstituted or substituted by one to three C$_1$-C$_4$-alkyl, C$_6$-C$_{10}$-aryl, C$_4$-C$_8$-cycloalkyl-C$_1$-C$_4$-alkyl, C$_6$-C$_{14}$-aryl-C$_1$-C$_4$-alkyl, C$_2$-C$_6$-alkyl, which is substituted by a hydroxyl group, 2,2,6,6-tetramethylpiperidine-4-yl, 1-(C$_1$-C$_8$-alkyl)-2,2,6,6-tetramethylpiperidine-4-yl or 1-(C$_1$-C$_8$-alkoxy)-2,2,6,6-tetramethylpiperidine-4-yl, or R'$_2$ and R'$_3$ form together with the nitrogen atom to which they are attached a 5-, 6- or 7-membered saturated heterocycle;
R"$_1$ and R"$_2$ are independently from each other H, C$_1$-C$_{22}$-alkyl, C$_2$-C$_{18}$-alkenyl, C$_4$-C$_8$-cycloalkyl, which is unsubstituted or substituted by one to three C$_1$-C$_4$-alkyl, C$_4$-C$_8$-cycloalkyl-C$_1$-C$_4$-alkyl, C$_6$-C$_{14}$-aryl-C$_1$-C$_4$-alkyl;
Z$_1$ is C$_2$-C$_{12}$-alkylene, C$_4$-C$_8$-cycloalkylene, C$_4$-C$_8$-cycloalkane-bis-(C$_1$-C$_4$-alkylene), C$_6$-C$_{14}$-arene-bis-(C$_1$-C$_4$-alkylene), C$_3$-C$_6$-alkylene, which is substituted by one or more hydroxyl groups, C$_4$-C$_{12}$-alkylene, which is interrupted by one or more oxygen atoms, hexahydro-furo[3,2-b]furane-3,6-diyl, C$_4$-C$_8$-alkylene, which is interrupted by a sulfur atom, 3-(C$_1$-C$_8$-alkyl)-3-azapentane-1,5-diyl, 4-(C$_1$-C$_8$-alkyl)-4-azaheptane-1,7-diyl or 1-ethyl-2,2,6,6-tetramethylpiperidine-4,2'-diyl; and
Z$_2$ is C$_2$-C$_{12}$-alkylene, C$_4$-C$_8$-cycloalkylene, C$_6$-C$_{14}$-arylene, C$_4$-C$_8$-cycloalkane-bis(C$_1$-C$_4$-alkylene), C$_6$-C$_{14}$-arene-bis-(C$_1$-C$_4$-alkylene), C$_4$-C$_{12}$-alkylene, which is interrupted by one or more oxygen atoms, 3-(C$_1$-C$_8$-alkyl)-3-azapentane-1,5-diyl or 4-(C$_1$-C$_8$-alkyl)-4-azaheptane-1,7-diyl.
Preferred is a compound of formula I, wherein
when n is 1
A is —C(=O)—OR'$_1$ or —C(=O)—N(R'$_2$)(R'$_3$);
when n is 2
A is —C(=O)—O—Z$_1$—O—C(=O)—, —C(=O)—N(R"$_1$)—Z$_2$—N(R"$_2$)—C(=O)— or piperazine-N,N'-bis-carbonyl;
when n is 3
A is C$_3$-C$_{12}$-alkane-tri-(oxycarbonyl);
when n is 4
A is C$_4$-C$_{16}$-alkane-tetra-(oxycarbonyl);
n is 1, 2, 3 or 4;
R$_1$, R$_2$, R$_3$, R$_4$, R$_5$, R$_6$, R$_7$, R$_8$, R$_9$ and R$_{10}$ are independently from each other H, C$_1$-C$_8$-alkyl, C$_4$-C$_8$-cycloalkyl, phenyl, C$_1$-C$_4$-alkoxy or halogen;
R'$_1$ is H, C$_1$-C$_{22}$-alkyl, C$_2$-C$_{18}$-alkenyl, C$_3$-C$_{12}$-alkine-yl, C$_4$-C$_8$-cycloalkyl, which is unsubstituted or substituted by one to three C$_1$-C$_4$-alkyl, C$_4$-C$_8$-cycloalkyl-C$_1$-C$_4$-alkyl, bicyclic or tricyclic C$_5$-C$_{20}$-alkyl, C$_6$-C$_{14}$-aryl-C$_1$-C$_4$-alkyl, C$_2$-C$_{12}$-alkyl, which is substituted by one or more hydroxyl groups, C$_4$-C$_{12}$-alkyl, which is interrupted by one or more oxygen atoms, C$_4$-C$_{18}$-alkyl, which is interrupted by one sulfur atom, 2,2,6,6-tetramethylpiperidine-4-yl, 1-(C$_1$-C$_8$-alkyl)-2,2,6,6-tetramethylpiperidine-4-yl or 1-(C$_1$-C$_8$-alkoxy)-2,2,6,6-tetramethylpiperidine-4-yl;
R'$_2$ and R'$_3$ are independently from each other H, C$_1$-C$_{22}$-alkyl, C$_2$-C$_{18}$-alkenyl, C$_4$-C$_8$-cycloalkyl, which is unsubstituted or substituted by one to three C$_1$-C$_4$-alkyl, C$_6$-C$_{10}$-aryl, C$_4$-C$_8$-cycloalkyl-C$_1$-C$_4$-alkyl, C$_6$-C$_{14}$-aryl-C$_1$-C$_4$-alkyl, C$_2$-C$_6$-alkyl, which is substituted by a hydroxyl group, 2,2,6,6-tetramethylpiperidine-4-yl, 1-(C$_1$-C$_8$-alkyl)-2,2,6,6-tetramethylpiperidine-4-yl or 1-(C$_1$-C$_8$-alkoxy)-2,2,6,6-tetramethylpiperidine-4-yl, or R'$_2$ and R'$_3$ form together with the nitrogen atom to which they are attached a 5-, 6- or 7-membered saturated heterocycle;
R"$_1$ and R"$_2$ are independently from each other H, C$_1$-C$_{22}$-alkyl, C$_2$-C$_{18}$-alkenyl, C$_4$-C$_8$-cycloalkyl, which is unsubstituted or substituted by one to three C$_1$-C$_4$-alkyl, C$_4$-C$_8$-cycloalkyl-C$_1$-C$_4$-alkyl, C$_6$-C$_{14}$-aryl-C$_1$-C$_4$-alkyl;

$Z_1$ is $C_2$-$C_{12}$-alkylene, $C_4$-$C_8$-cycloalkylene, $C_4$-$C_8$-cycloalkane-bis-($C_1$-$C_4$-alkylene), $C_6$-$C_{14}$-arene-bis-($C_1$-$C_4$-alkylene), $C_3$-$C_6$-alkylene, which is substituted by one or more hydroxyl groups, $C_4$-$C_{12}$-alkylene, which is interrupted by one or more oxygen atoms, $C_4$-$C_8$-alkylene, which is interrupted by a sulfur atom; and $Z_2$ is $C_2$-$C_{12}$-alkylene, $C_4$-$C_8$-cycloalkylene, $C_6$-$C_{14}$-arylene, $C_4$-$C_8$-cycloalkane-bis($C_1$-$C_4$-alkylene), $C_6$-$C_{14}$-arene-bis-($C_1$-$C_4$-alkylene), $C_4$-$C_{12}$-alkylene, which is interrupted by one or more oxygen atoms, 3-($C_1$-$C_8$-alkyl)-3-azapentane-1,5-diyl or 4-($C_1$-$C_8$-alkyl)-4-azaheptane-1,7-diyl.

Preferred is a composition, which comprise a compound of formula I, wherein
when n is 1
A is —C(=O)—OR'$_1$, —C(=O)—N(R'$_2$)(R'$_3$), —CN, phenyl, which is unsubstituted or substituted by one to three $C_1$-$C_8$-alkyl or $C_1$-$C_4$-alkoxy, —H or —SO$_2$-phenyl;
when n is 2
A is —C(=O)—O—$Z_1$—O—C(=O)—, —C(=O)—N(R"$_1$)—$Z_2$—N(R"$_2$)—C(=O)— or piperazine-N,N'-biscarbonyl;
when n is 3
A is propane-1,2,3-tri-(oxycarbonyl), 2-methyl-propane-1,2,3-tri-(oxycarbonyl), 2-methyl-butane-1,2,1'-tri-(oxycarbonyl), 2,2-dimethyl-butane-1,1',1"-tri-(oxycarbonyl), 2,2-dimethyl-pentane-1,1',1"-tri-(oxycarbonyl), 3-ethyl-3-azapentane-1,5,2'-tri-(oxycarbonyl);
when n is 4
A is 2,2-dimethyl-propane-1,3,1',1"-tetra-(oxycarbonyl);
n is 1, 2, 3 or 4;
$R_1$, $R_2$, $R_3$, $R_4$, $R_5$, $R_6$, $R_7$, $R_8$, $R_9$ and $R_{10}$ are independently from each other H, $C_1$-$C_8$-alkyl, phenyl or $C_1$-$C_4$-alkoxy with the proviso that at least $R_1$ or $R_5$ is H and at least $R_6$ or $R_{10}$ is H;
R'$_1$ is H, $C_1$-$C_{22}$-alkyl, $C_2$-$C_{18}$-alkenyl, $C_5$-$C_7$-cycloalkyl, which is unsubstituted or substituted by one $C_1$-$C_4$-alkyl, $C_5$-$C_7$-cycloalkyl-$C_1$-$C_4$-alkyl, $C_6$-$C_{10}$-aryl-$C_1$-$C_4$-alkyl, $C_4$-$C_{12}$-alkyl, which is interrupted by one or more oxygen atoms, 2,2,6,6-tetramethylpiperidine-4-yl, 1-($C_1$-$C_6$-alkyl)-2,2,6,6-tetramethylpiperidine-4-yl or 1-($C_1$-$C_6$-alkoxy)-2,2,6,6-tetramethylpiperidine-4-yl;
R'$_2$ and R'$_3$ are independently from each other H, $C_1$-$C_{22}$-alkyl, $C_2$-$C_{18}$-alkenyl, $C_5$-$C_7$-cycloalkyl, which is unsubstituted or substituted by one $C_1$-$C_4$-alkyl, $C_5$-$C_{10}$-aryl, $C_5$-$C_7$-cycloalkyl-$C_1$-$C_4$-alkyl, $C_6$-$C_{10}$-aryl-$C_1$-$C_4$-alkyl, 2,2,6,6-tetramethylpiperidine-4-yl, 1-($C_1$-$C_6$-alkyl)-2,2,6,6-tetramethylpiperidine-4-yl or 1-($C_1$-$C_6$-alkoxy)-2,2,6,6-tetramethylpiperidine-4-yl, or R'$_2$ and R'$_3$ form together with the nitrogen atom to which they are attached a pyrrolidine, a piperidine or a morpholine;
R"$_1$ and R"$_2$ independently from each other H, $C_1$-$C_{22}$-alkyl, $C_2$-$C_{18}$-alkenyl, $C_5$-$C_7$-cycloalkyl, which is unsubstituted or substituted by one $C_1$-$C_4$-alkyl, $C_5$-$C_7$-cycloalkyl-$C_1$-$C_4$-alkyl, $C_6$-$C_{10}$-aryl-$C_1$-$C_4$-alkyl;
$Z_1$ is $C_2$-$C_{12}$-alkylene, $C_5$-$C_7$-cycloalkylene, $C_5$-$C_7$-cycloalkane-bis-($C_1$-$C_4$-alkylene), $C_6$-$C_{10}$-arene-bis-($C_1$-$C_4$-alkylene), $C_3$-$C_6$-alkylene, which is substituted by one or more hydroxyl groups, $C_4$-$C_{12}$-alkylene, which is interrupted by one or more oxygen atoms, $C_4$-$C_8$-alkylene, which is interrupted by a sulfur atom, 3-($C_1$-$C_4$-alkyl)-3-azapentane-1,5-diyl, 4-($C_1$-$C_4$-alkyl)-4-azaheptane-1,7-diyl or 1-ethyl-2,2,6,6-tetramethylpiperidine-4,2'-diyl; and
$Z_2$ is $C_2$-$C_{12}$-alkylene, $C_5$-$C_7$-cycloalkylene, $C_6$-$C_{14}$-arylene, $C_5$-$C_7$-cycloalkane-bis-($C_1$-$C_4$-alkylene), $C_6$-$C_{19}$-arene-bis-($C_1$-$C_4$-alkylene), $C_4$-$C_{12}$-alkylene, which is interrupted by one or more oxygen atoms, 3-($C_1$-$C_4$-alkyl)-3-azapentane-1,5-diyl or 4-($C_1$-$C_4$-alkyl)-4-azaheptane-1,7-diyl.

Preferred is a composition, which comprise a compound of formula I, wherein
when n is 1
A is —C(=O)—OR'$_1$, —C(=O)—N(R'$_2$)(R'$_3$), —CN, phenyl, which is unsubstituted or substituted by one or two $C_1$-$C_8$-alkyl or $C_1$-$C_4$-alkoxy, —H or —SO$_2$-phenyl;
when n is 2
A is —C(=O)—O—$Z_1$—O—C(=O)—, —C(=O)—N(R"$_1$)—$Z_2$—N(R"$_2$)—C(=O)— or piperazine-N,N'-biscarbonyl;
when n is 3
A is propane-1,2,3-tri-(oxycarbonyl), 2-methyl-propane-1,2,3-tri-(oxycarbonyl), 2-methyl-butane-1,2,1'-tri-(oxycarbonyl), 2,2-dimethyl-butane-1,1',1"-tri-(oxycarbonyl), 2,2-dimethyl-pentane-1,1',1"-tri-(oxycarbonyl);
when n is 4
A is 2,2-dimethyl-propane-1,3,1',1"-tetra-(oxycarbonyl);
n is 1, 2, 3 or 4;
$R_1$, $R_2$, $R_4$, $R_5$, $R_6$, $R_7$, $R_9$ and $R_{10}$ are H;
$R_3$ and $R_8$ are independently from each other H, $C_1$-$C_8$-alkyl, $C_4$-$C_8$-cycloalkyl, phenyl, $C_1$-$C_4$-alkoxy or halogen;
R'$_1$ is H, $C_1$-$C_{22}$-alkyl, $C_2$-$C_{18}$-alkenyl, $C_5$-$C_7$-cycloalkyl, which is unsubstituted, $C_5$-$C_7$-cycloalkyl-$C_1$-$C_4$-alkyl, phenyl-$C_1$-$C_4$-alkyl, $C_4$-$C_{12}$-alkyl, which is interrupted by one or more oxygen atoms, 2,2,6,6-tetramethylpiperidine-4-yl, 1-($C_1$-$C_8$-alkyl)-2,2,6,6-tetramethylpiperidine-4-yl or 1-($C_1$-$C_6$-alkoxy)-2,2,6,6-tetramethylpiperidine-4-yl;
R'$_2$ and R'$_3$ are independently from each other H, $C_1$-$C_{22}$-alkyl, $C_2$-$C_{18}$-alkenyl, $C_5$-$C_7$-cycloalkyl, which is unsubstituted, $C_5$-$C_{10}$-aryl, $C_5$-$C_7$-cycloalkyl-$C_1$-$C_4$-alkyl, phenyl-$C_1$-$C_4$-alkyl, 2,2,6,6-tetramethylpiperidine-4-yl, 1-($C_1$-$C_8$-alkyl)-2,2,6,6-tetramethylpiperidine-4-yl or 1-($C_1$-$C_6$-alkoxy)-2,2,6,6-tetramethylpiperidine-4-yl, or R'$_2$ and R'$_3$ form together with the nitrogen atom to which they are attached a pyrrolidine, a piperidine or a morpholine;
R"$_1$ and R"$_2$ are independently from each other H, $C_1$-$C_{22}$-alkyl, $C_2$-$C_{18}$-alkenyl, $C_5$-$C_7$-cycloalkyl, which is unsubstituted, $C_5$-$C_7$-cycloalkyl-$C_1$-$C_4$-alkyl or phenyl-$C_1$-$C_4$-alkyl;
$Z_1$ is $C_2$-$C_{12}$-alkylene, $C_5$-$C_7$-cycloalkylene, $C_5$-$C_7$-cycloalkane-bis-($C_1$-$C_4$-alkylene), benzene-bis-($C_1$-$C_4$-alkylene), $C_3$-$C_6$-alkylene, which is substituted by one or more hydroxyl groups, $C_4$-$C_{12}$-alkylene, which is interrupted by one or more oxygen atoms, $C_4$-$C_8$-alkylene, which is interrupted by a sulfur atom, 3-($C_1$-$C_4$-alkyl)-3-azapentane-1,5-diyl, 4-($C_1$-$C_4$-alkyl)-4-azaheptane-1,7-diyl or 1-ethyl-2,2,6,6-tetramethylpiperidine-4,2'-diyl; and
$Z_2$ is $C_2$-$C_{12}$-alkylene, $C_5$-$C_7$-cycloalkylene, $C_6$-$C_{14}$-arylene, $C_5$-$C_7$-cycloalkane-bis($C_1$-$C_4$-alkylene), benzene-bis-($C_1$-$C_4$-alkylene), $C_4$-$C_{12}$-alkylene, which is interrupted by one or more oxygen atoms, 3-($C_1$-$C_4$-alkyl)-3-azapentane-1,5-diyl or 4-($C_1$-$C_4$-alkyl)-4-azaheptane-1,7-diyl.

Preferred is a composition, which comprise a compound of formula I, wherein
n is 1,
A is —CN, phenyl or —H; and
$R_1$, $R_2$, $R_3$, $R_4$, $R_5$, $R_6$, $R_7$, $R_8$, $R_9$ and $R_{10}$ are independently from each other H, $C_1$-$C_8$-alkyl, $C_4$-$C_8$-cycloalkyl, phenyl, $C_1$-$C_4$-alkoxy or halogen.

Preferred is a composition, which comprise a compound of formula I, wherein at formula I when n is 1

A is —C(=O)—OR'$_1$, —C(=O)—N(R'$_2$)(R'$_3$), —CN, phenyl, —H or —SO$_2$-phenyl;

when n is 2

A is —C(=O)—O—Z$_1$—O—C(=O)—;

n is 1 or 2;

R$_1$, R$_2$, R$_4$, R$_5$, R$_6$, R$_7$, R$_9$ and R$_{10}$ are H;

R$_3$ and R$_8$ are independently from each other H or C$_1$-C$_4$-alkoxy;

R'$_1$ is H, C$_1$-C$_{12}$-alkyl, C$_5$-C$_7$-cycloalkyl, which is unsubstituted, phenyl-C$_1$-C$_4$-alkyl, 1-(C$_1$-C$_6$-alkyl)-2,2,6,6-tetramethylpiperidine-4-yl or 1-(C$_1$-C$_6$-alkoxy)-2,2,6,6-tetramethylpiperidine-4-yl;

R'$_2$ and R'$_3$ are independently from each other H, C$_1$-C$_{12}$-alkyl, C$_5$-C$_7$-cycloalkyl, which is unsubstituted, C$_6$-C$_{10}$-aryl, phenyl-C$_1$-C$_4$-alkyl, 1-(C$_1$-C$_6$-alkyl)-2,2,6,6-tetramethylpiperidine-4-yl or 1-(C$_1$-C$_6$-alkoxy)-2,2,6,6-tetramethylpiperidine-4-yl, or R'$_2$ and R'$_3$ form together with the nitrogen atom to which they are attached a pyrrolidine, a piperidine or a morpholine; and Z$_1$ is C$_5$-C$_7$-cycloalkylene.

Preferred is a composition, which comprise a compound of formula I, wherein when n is 1

A is —C(=O)—OCH$_3$, —CN, phenyl or —H;

when n is 2

A is —C(=O)—O—Z$_1$—O—C(=O)—;

n is 1 or 2;

R$_1$, R$_2$, R$_3$, R$_4$, R$_5$, R$_6$, R$_7$, R$_8$, R$_9$ and R$_{10}$ are H; and Z$_1$ is cyclo-hexane-1,4-diyl.

The organic material of the present invention is susceptible to oxidative, thermal or light-induced degradation. Examples of an organic material are:

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylenepropylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

A special copolymer of two monoolefins is a pipe grade polypropylene random copolymer, which is obtainable from the polymerization of more than 90% by weight of propylene and of less than 10% by weight, typically between 2 and 6% by weight, of ethylene.

4. Hydrocarbon resins (for example C$_5$-C$_9$) including hydrogenated modifications thereof (e.g. tackifiers) and mixtures of polyalkylenes and starch. Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrite/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes, for example polyurethanes synthesized from a polyol and an aliphatic or aromatic polyisocyanate such as polyurethanes derived from hydroxyl-terminated polyethers, polyesters or polybutadienes on the one hand and aliphatic or aromatic polyisocyanates on the other, as well as precursors thereof.

Hydroxyl-terminated polyethers are known and are prepared, for example, by polymerizing epoxides such as ethylene oxide, propylene oxide, butylene oxide, tetrahydrofuran, styrene oxide or epichlorohydrin with themselves, for example in the presence of $BF_3$, or by addition reaction of these epoxides, alone or as a mixture or in succession, with starting components containing reactive hydrogen atoms, such as water, alcohols, ammonia or amines, for example ethylene glycol, propylene 1,3- and 1,2-glycol, trimethylolpropane, 4,4'-dihydroxydiphenylpropane, aniline, ethanolamine or ethylenediamine. Sucrose polyethers are also suitable in accordance with the invention. In many cases preference is given to those polyethers which predominantly (up to 90% by weight, based on all the OH groups present in the polyether) contain primary OH groups. Furthermore, polyethers modified by vinyl polymers, as are formed, for example, by polymerizing styrene and acrylonitrile in the presence of polyethers, are suitable, as are polybutadienes containing OH groups.

In particular, a polyol compound has a molecular weight of 400-10000, especially 800 to 10000, and is a polyhydroxy compound, especially containing from 2 to 8 hydroxyl groups, especially from 2 to 4.

Suitable polyisocyanates are aliphatic or aromatic, for example ethylene diisocyanate, 1,4-tetramethylene diisocyanate, 1,6-hexamethylene diisocyanate, 1,12-dodecane diisocyanate, cyclobutane 1,3-diisocyanate, cyclohexane 1,3- and -1,4-diisocyanate and also any desired mixtures of these isomers, 1-isocyanato-3,3,5-trimethyl-5-isocyanatomethylcyclohexane, 2,4- and 2,6-hexahydrotolylene diisocyanate and also any desired mixtures of these isomers, hexahydro-1,3- and/or -1,4-phenylene diisocyanate, perhydro-2,4'- and/or -4,4'-diphenylmethanediisocyanate, 1,3- and 1,4-phenylene diisocyanate, 2,4- and 2,6-tolylene diisocyanate, and also any desired mixtures of these isomers, diphenylmethane 2,4'- and/or -4,4'-diisocyanate, naphthylene 1,5-diisocyanate, triphenylmethane 4,4',4"-triisocyanate, polyphenyl-polymethylene polyisocyanates as are obtained by aniline-formaldehyde condensation followed by phosgenization, m- and p-isocyanatophenylsulfonyl isocyanates, perchlorinated aryl polyisocyanates, polyisocyanates containing carbodiimide groups, polyisocyanates containing allophanate groups, polyisocyanates containing isocyanurate groups, polyisocyanates containing urethane groups, polyisocyanates containing acylated urea groups, polyisocyanates containing biuret groups, polyisocyanates containing ester groups, reaction products of the abovementioned isocyanates with acetals, and polyisocyanates containing polymeric fatty acid radicals.

It is also possible to employ the isocyanate group-containing distillation residues, as they are or dissolved in one or more of the abovementioned polyisocyanates, which are obtained in the course of the industrial preparation of isocyanates. It is additionally possible to use any desired mixtures of the abovementioned polyisocyanates.

Preferred are 2,4- or 2,6-tolylene diisocyanate and any desired mixtures of these isomers ("TDI"), polyphenyl-polymethylene-polyisocyanates as prepared by aniline-formaldehyde condensation followed by phosgenization ("crude MDI") or polyisocyanates containing carbodiimide, urethane, allophanate, isocyanurate, urea or biuret groups ("modified polyisocyanates").

The polyurethanes can be homogeneous polyurethanes or cellular.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).
17. Polyureas, polyimides, polyamide-imides, polyetherimides, polyesterimides, polyhydantoins and polybenzimidazoles.
18. Polyesters derived from dicarboxylic acids and diols and/or from hydroxycarboxylic acids or the corresponding lactones or lactides, for example polyethylene terephthalate, polybutylene terephthalate, poly-1,4-dimethylolcyclohexane terephthalate, polyalkylene naphthalate and polyhydroxybenzoates as well as copolyether esters derived from hydroxyl-terminated polyethers, and also polyesters modified with polycarbonates or MBS. Copolyesters may comprise, for example—but are not limited to—polybutylenesuccinate/terephtalate, polybutyleneadipate/terephthalate, polytetramethyleneadipate/terephthalate, polybutylensuccinate/adipate, polybutylensuccinate/carbonate, poly-3-hydroxybutyrate/octanoate copolymer, poly-3-hydroxybutyrate/hexanoate/decanoate terpolymer. Furthermore, aliphatic polyesters may comprise, for example—but are not limited to—the class of poly(hydroxyalkanoates), in particular, poly(propiolactone), poly(butyrolactone), poly(pivalolactone), poly(valerolactone) and poly(caprolactone), polyethylenesuccinate, polypropylenesuccinate, polybutylenesuccinate, polyhexamethylenesuccinate, polyethyleneadipate, polypropyleneadipate, polybutyleneadipate, polyhexamethyleneadipate, polyethyleneoxalate, polypropyleneoxelate, polybutyleneoxalate, polyhexamethyleneoxalate, polyethylenesebacate, polypropylenesebacate, polybutylenesebacate and polylactic acid (PLA) as well as corresponding polyesters modified with polycarbonates or MBS. The term "polylactic acid (PLA)" designates a homo-polymer of preferably poly-L-lactide and any of its blends or alloys with other polymers; a co-polymer of lactic acid or lactide with other monomers, such as hydroxy-carboxylic acids, like for example glycolic acid, 3-hydroxy-butyric acid, 4-hydroxy-butyric acid, 4-hydroxy-valeric acid, 5-hydroxy-valeric acid, 6-hydroxy-caproic acid and cyclic forms thereof; the terms "lactic acid" or "lactide" include L-lactic acid, D-lactic acid, mixtures and dimers thereof, i.e. L-lactide, D-lactide, meso-lacide and any mixtures thereof.
19. Polycarbonates and polyester carbonates.
20. Polyketones.
21. Polysulfones, polyether sulfones and polyether ketones.
22. Crosslinked polymers derived from aldehydes on the one hand and phenols, ureas and melamines on the other hand, such as phenol/formaldehyde resins, urea/formaldehyde resins and melamine/formaldehyde resins.
23. Drying and non-drying alkyd resins.
24. Unsaturated polyester resins derived from copolyesters of saturated and unsaturated dicarboxylic acids with polyhydric alcohols and vinyl compounds as crosslinking agents, and also halogen-containing modifications thereof of low flammability.
25. Crosslinkable acrylic resins derived from substituted acrylates, for example epoxy acrylates, urethane acrylates or polyester acrylates.
26. Alkyd resins, polyester resins and acrylate resins crosslinked with melamine resins, urea resins, isocyanates, isocyanurates, polyisocyanates or epoxy resins.
27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.
28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
29. Blends of the aforementioned polymers (polyblends), for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.
30. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
31. Aqueous emulsions of natural or synthetic rubber, e.g. natural latex or latices of carboxylated styrene/butadiene copolymers.

A polymer can be natural, semi-synthetic or synthetic. A natural polymer is isolated from a natural source without further synthetic modifications. A synthetic polymer does not contain a polymer part isolated from a natural source. A semi-synthetic polymer contains at least one natural polymer part, wherein the natural polymer part can be synthetically modified and/or reacted with monomers to form the semi-synthetic polymer.

A polymer can be thermoplastic, i.e. it can be shaped into a new form at an elevated temperature, for example at a temperature in the range from 150° C. to 340° C.

Preferred is a composition, which comprises as component a) an organic material, wherein the organic material is selected from the group consisting of a polymer, a wax, a mineral oil and a fat, and a component b).

Preferred is a composition, which comprises as component a) a polymer, in particular a semi-synthetic or synthetic polymer, and as component b) a compound of formula I.

Preferred is a composition, which comprises as component a) a semi-synthetic or synthetic polymer.

Preferred is a composition, which comprises as component a) a thermoplastic polymer.

Preferred is a composition, which comprises as component a) a polymer, which is synthetic and thermoplastic.

Preferred is a composition, which comprises as component a) a polyolefin, a polyether polyol or a polyurethane.

The employed amount of component b) in regard to component a) varies with the particular organic material and the desired degree of protection.

Preferred is a composition, which comprises a component a) and a component b), wherein component b) is contained in an amount of 0.0005% to 10%, in particular from 0.001 to 2%, especially from 0.005 to 1%, based on the weight of component a).

Optionally, a composition comprising a component a) and a component b) contains as component c) a further additive.

A further additive can be selected from the following list:
1. Antioxidants
1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example 2,6-di-nonyl-4-methylphenol, 2,4-dimethyl-6-(1'-methyl-undec-1'-yl)phenol, 2,4-dimethyl-6-(1'-methyl heptadec-1'-yl) phenol, 2,4-dimethyl-6-(1'-methyltridec-1'-yl)phenol, 2,4-dimethyl-6-(1'-methyl-1'-tetradecyl-methyl)-phenol and mixtures thereof.
1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecyl-thiomethyl-4-nonyl phenol.
1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.
1.4. Tocopherols, for example α-tocopherol, β-tocopherol, γ-tocopherol, δ-tocopherol and mixtures thereof (vitamin E).
1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methyl phenol), 4,4'-thiobis(3,6-di-sec-amylphenol), 4,4'-bis(2,6-dimethyl-4-hydroxyphenyl)disulfide.
1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)-butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)-propane, 2,2-bis-(5-tert-butyl-4-hydroxy-2-methylphenyl)-4-n-dodecylmercaptobutane, 1,1,5,5-tetra(5-tert-butyl-4-hydroxy-2-methyl phenyl) pentane.
1.7. O—, N— and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxy-benzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzyl-mercaptoacetate.
1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methyl benzyl) malonate, di-dodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.
1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.
1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-d i-tert-butyl-4-hydroxyphenylpropionyl)-hexahydro-1,3,5-triazine, 1,3,5-tris(3,5-dicyclohexyl-4-hydroxybenzypisocyanurate.
1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.
1.12. Acylaminophenols, for example 4-hydroxylauranilide, 4-hydroxystearanilide, octyl N-(3,5-di-tert-butyl-4-hydroxyphenyl)carbamate.
1.13. Esters of β-(3,5-di-tert-butyl-4-hydroxyphenyl)propionic acid with mono- or polyhydric alcohols, for example with methanol, ethanol, n-octanol, i-octanol, octadecanol, a mixture of linear and branched $C_{13}$-$C_{15}$-alkanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxylethyl)isocyanurate, N,N'-bis-(hydroxylethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl) propionic acid with mono- or polyhydric alcohols, for example with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris-(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]undecane.

1.15. Esters of β-(3,5-dicyclohexyl-4-hydroxyphenyl)propionic acid with mono- or polyhydric alcohols, for example with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]-octane.

1.16. Esters of 3,5-di-tert-butyl-4-hydroxyphenyl acetic acid with mono- or polyhydric alcohols, for example with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl)propionic acid, for example N,N'-bis(3,5-di-tert-butyl-4-hydroxyphenylpropionyl)hexamethylenediamide, N,N'-bis(3,5-di-tert-butyl-4-hydroxyphenylpropionyl) trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]-propionyloxy)ethyl] oxamide (Naugard XL-1®, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl) diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl) amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]-ethane, 1,2-bis(phenylamino)propane, (o-tolyl)biguanide, bis[4-(1,3'-dimethylbutyl)-phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene, N,N-bis(2,2,6,6-tetramethylpiperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tertamyl-2'-hydroxyphenyl)benzotriazole, 2-(3',5'-bis(α,α-dimethylbenzyl)-2'-hydroxyphenyl)benzotriazole, 2-(3'-tert-butyl-2'-hydroxy-5'-(2-octyloxycarbonylethyl) phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)-phenyl)-5-chlorobenzotriazole, 2-(3'-tert-butyl-2'-hydroxy-5'-(2-methoxycarbonylethyl)-phenyl)benzotriazole, 2-(3'-tert-butyl-2'-hydroxy-5'-(2-octyloxycarbonylethyl)phenyl)-benzotriazole, 2-(3'-tert-butyl-5'-[2-(2-ethylhexyloxy)carbonylethyl]-2'-hydroxyphenyl)-benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylenebis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300;

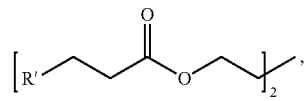

where R'=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)phenyl]benzotriazole; 2-[2'-hydroxy-3'-(1,1,3,3-tetramethylbutyl)-5'-(α,α-dimethylbenzyl)phenyl] benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butyl-phenyl salicylate, phenyl salicylate, octylphenyl salicylate, dibenzoyl resorcinol, bis(4-tert-butyl benzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-p-methyl-p-methoxycinnamate, methyl α-carbomethoxy-p-methoxycinnamate, N-(β-carbomethoxy-(β-cyanovinyl)-2-methylindoline and neopentyl tetra(α-cyano-β,β-diphenylacrylate).

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)-sebacate, bis(2,2,6,6-tetramethyl-4-piperidyl)succinate, bis(1,2,2,6,6-pentamethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyphexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperid-4-yl)sebacate, bis(1-octyloxy-2,2,6,6-tetramethylpiperid-4-yl)succinate, bis-[2,2,6,6-tetramethyl-1-(undecyloxy)-piperidin-4-yl]carbonate, linear or cyclic condensates of N,N'-bis(2,2,6,6-tetramethyl-4-piperidyl)-hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyphexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [19226864-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)-ethene, N,N'-bis-formyl-N,N'-bis(2,2,6,6-tetramethyl-4-piperidyphexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine, a mixture of oligomeric compounds which are the formal condensation products of N,N'-bis-(2,2,6,6-tetramethyl-1-propoxy-piperidin-4-yl)-hexane-1,6-diamine and 2,4-dichloro-6-{n-butyl-(2,2,6,6-tetramethyl-1-propoxy-piperidin-4-yl)-amino}-[1,3,5]triazine end-capped with 2-chloro-4,6-bis(di-n-butylamino)-[1,3,5]triazine, a mixture of oligomeric compounds which are the formal condensation products of N,N'-bis-(2,2,6,6-tetramethyl-piperidin-4-yl)-hexane-1,6-diamine and 2,4-dichloro-6-{n-butyl-(2,2,6,6-tetramethyl-piperidin-4-yl)-amino}-[1,3,5]triazine end-capped with 2-chloro-4,6-bis-(di-n-butylamino)-[1,3,5]triazine, 2,4-bis[N-(1-cyclohexyloxy-2,2,6,6-tetramethylpiperidine-4-yl)-N-butylamino]-6-(2-hydroxyethyl)amino-1,3,5-triazine, 1-(2-hydroxy-2-methylpropoxy)-4-octadecanoyloxy-2,2,6,6-tetramethylpiperidine, 5-(2-ethylhexanoyl)oxymethyl-3,3,5-trimethyl-2-morpholinone, Sanduvor (Clariant; CAS Reg. No. 106917-31-1], 5-(2-ethylhexanoyl)-oxymethyl-3,3,5-trimethyl-2-morpholinone, the reaction product of 2,4-bis-[(1-cyclo-hexyloxy-2,2,6,6-piperidine-4-yl)butylamino]-6-chloro-s-triazine with N,N'-bis-(3-aminopropyl)ethylenediamine), 1,3,5-tris(N-cyclohexyl-N-(2,2,6,6-tetramethylpiperazine-3-one-4-yl)amino)-s-triazine, 1,3,5-tris(N-cyclohexyl-N-(1,2,2,6,6-pentamethylpiperazine-3-one-4-yl)-amino)-s-triazine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyhoxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5- triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]-phenyl}-4,6-bis-(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)-thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,4-di-cumylphenyl)pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)pentaerythritol diphosphite, bis(2,4,6-tris(tert-butyl phenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl)methyl phosphite, bis(2,4-di-tert-butyl-6-methylphenyl)ethyl phosphite, 6-fluoro-2,4,8,10-tetra-tert-butyl-12-methyldibenz[d,g]-1,3,2-dioxaphosphocin, 2,2',2''-nitrilo-[triethyltris(3,3',5,5'-tetra-tert-butyl-1,1'-biphenyl-2,2'-diyl) phosphite], 2-ethylhexyl-(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

The following phosphites are especially preferred:

Tris(2,4-di-tert-butylphenyl) phosphite (Irgafos 168, RTM BASF), tris(nonylphenyl) phosphite,

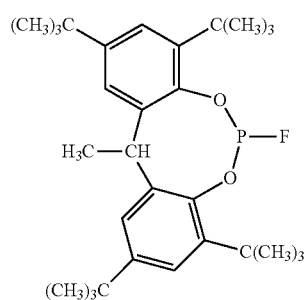
(A)

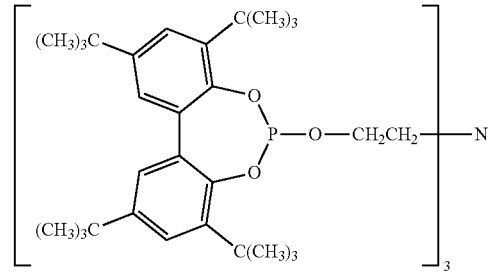
(B)

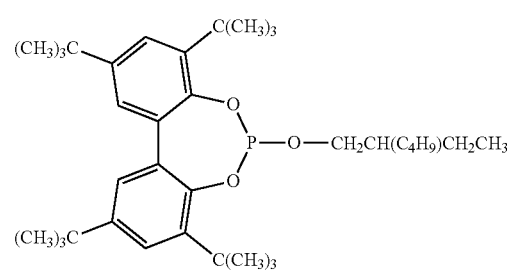
(C)

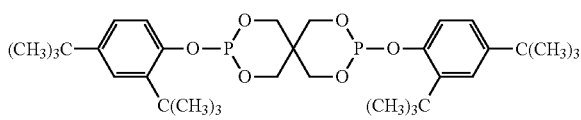
(D)

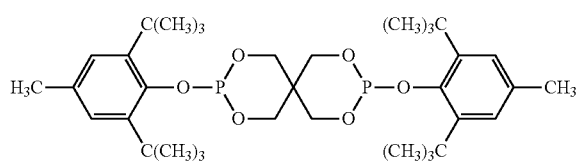
(E)

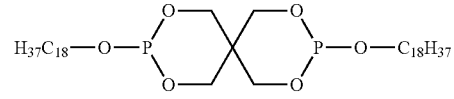
(F)

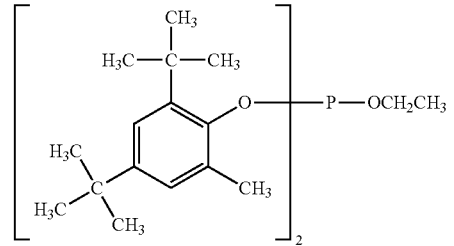
(G)

5. Hydroxylamines and amine N-oxides, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine or N,N-bis-(hydrogenated rape-oil alkyl)-N-methyl-amine N-oxide.

6. Nitrones, for example N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-heptadecylnitrone, N-octadecyl-alpha-hexadecylnitrone, nitrone derived from N,N-dialkylhydroxylamine derived from hydrogenated tallow amine.
7. Thiosynergists, for example dilauryl thiodipropionate, dimistryl thiodipropionate, distearyl thiodipropionate and pentaerythritol tetrakis-[3-(n-lauryl)-propionic acid ester].
8. Peroxide scavengers, for example esters of α-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecyl mercapto)propionate.
9. Polyamide stabilizers, for example copper salts in combination with iodides and/or phosphorus compounds and salts of divalent manganese.
10. Acid scavengers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate and zinc pyrocatecholate.
11. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)phenyl]-5,7-di-tert-butylbenzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]-phenyl) benzofuran-2-one], 5,7-di-tert-butyl-3-(4-ethoxyphenyl) benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one and 3-(2-acetoxy-4-(1,1,3,3-tetramethyl-butyl)-phenyl)-5-(1,1,3,3-tetramethyl-butyl)-benzofuran-2-one.
12. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers), Irgaclear XT 386 (RTM BASF), 1,3:2,4-bis(3',4'-dimethylbenzylidene)-sorbitol, 1,3:2,4-di(paramethyldibenzylidene)-sorbitol, and 1,3:2,4-di(benzylidene) sorbitol.
13. Fillers and reinforcing agents, for example calcium carbonate, silicates, glass fibres, glass beads, asbestos, talc, kaolin, bentonite, mica, hydrotalcite, barium sulfate, metal oxides and hydroxides, carbon black, graphite, wood flour and flours or fibers of other natural products, synthetic fibers.
14. Other additives, for example plasticisers, lubricants, rheology additives, catalysts, flow-control agents, optical brighteners, flameproofing agents, antistatic agents and blowing agents.

Preferred is a composition, which comprises a component a), a component b) and as component c) a further additive.

Preferred is a composition, wherein the weight ratio of component b) to component c) is from 10:1 to 1:30, in particular from 4:1 to 1:20, especially from 2:1 to 1:10, and wherein the overall amount of component b) and component c) is below 50% by weight of component a).

Preferred is a composition, which comprises as component c) a further additive selected from the group consisting of an antioxidant, an UV absorber, a hindered amine light stabilizer, a nickel compound, a metal deactivator, a phosphite or phosphonite, a hydroxylamine or amine N-oxide, a thiosynergist, a peroxide scavenger, a nucleating agent and a filler or reinforcing agent.

Preferred is a composition, which comprises as component c) a further additive selected from the group consisting of a phosphite or phosphonite, an acid scavenger, a phenolic antioxidant and an aminic antioxidant.

Preferred is a composition, which comprises as component c) a phenolic antioxidant.

Preferred is a composition, which comprises as component c) a phenolic antioxidant, which is an ester of β-(3,5-di-tert-butyl-4-hydroxyphenyl)propionic acid.

Optionally, a composition comprising a component a), a component b) and a component c) contains as component d) a second further additive.

Preferred is a composition, which comprises a component a), a component b), as component c) a further additive and as component d) a second further additive.

Preferred is a composition, wherein the weight ratio of component b) to component d) is from 10:1 to 1:30, in particular from 4:1 to 1:20, especially from 2:1 to 1:10, and wherein the overall amount of component b), component c) and component d) is below 50% by weight of component a).

Preferred is a composition, which comprises a component a), a component b), as component c) a further additive, which is selected from the group consisting of a phosphite or phosphonite, an acid scavenger, a phenolic antioxidant and an aminic antioxidant, and as component d) a second further additive.

Preferred is a composition, which comprises a component a), a component b), a component c) and a component d), wherein component c) and component d) are independently from each other a phosphite or phosphonite, an acid scavenger, a phenolic antioxidant or an aminic antioxidant.

Preferred is a composition, which comprises a component a), a component b), as component c) a phenolic antioxidant and as component d) a phosphite or phosphonite.

Preferred is a composition, which comprises a component a), a component b), as component c) a phenolic antioxidant and as component d) an aminic antioxidant.

The above described preferences for a compound of formula I and an organic material susceptible to oxidative, thermal or light-induced degradation apply also to the further embodiments of the invention. This applies also to the optional further additive and the optional second further additive.

A further embodiment of the invention relates to a process for protection of an organic material susceptible to oxidative, thermal or light-induced degradation, i.e. component a), which comprises the step of incorporation into or application onto an organic material, a compound of formula I, i.e. component b).

The incorporation or application of component b) can be carried out in a processing apparatus, in particular a heatable container equipped with a stirrer, which can preferably be closed. A heatable container equipped with a stirrer is for example a kneader, extruder, mixer or stirred vessel. Specific examples thereof are a single-screw extruder, contrarotating and corotating twin-screw extruder, planetary-gear extruder, ring extruder or co-kneader. It is also possible to use a processing apparatus, which contains at least one gas removal compartment to which a vacuum can be applied and/or which can be set under an atmosphere, wherein the oxygen content is low or oxygen is absent. Component b) can be added directly into the processing apparatus.

Component b) can be incorporated or applied to at any stage of processing of component a), in particular prior to or during a shaping operation of component a) in the processing apparatus.

Component b) can be incorporated or applied in the form of a dry powder, in the form of a melt, in encapsulated form such as encapsulation in a wax or polymer or in the form of a wet mixture such as a solution, dispersion or suspension for example in an inert solvent, water or oil. A dispersing or suspension agent can be present in the case of a wet mixture of component b).

Component b) can also be incorporated or applied by spraying onto component a).

In case that component a) is a polymer, a further possibility for incorporation or application of component b) to component a) is addition before, during or directly after the polymerization of the corresponding starting materials, e.g. monomers, of component a). For example, spraying during the deactivation of the polymerization catalysts is particularly advantageous. If crosslinking takes place during formation of component a), incorporation or application prior to crosslinking is preferred.

In case that component a) is a polymer, the process of incorporation or application is preferably a moulding process, in particular an injection-moulding, blow-moulding, compression-moulding, roto-moulding, slush-moulding or extrusion-moulding.

Preferred is a process, wherein the incorporation or application takes place at a temperature in the range from 150 to 340° C., in particular from 180° C. to 330° C., especially from 190° C. to 320° C.

Preferred is a process, wherein component b) is incorporated or applied to in an extruder during processing of component a).

In case of a further additive, i.e. component c) or components c) and d), component b) and the further additive can be incorporated into or applied onto component a) individually or mixed with one another. If desired, the individual components can be mixed with one another before incorporation into component a) for example by dry blending, compaction, melting, encapsulation by a wax or polymer or as wet mixture in the form of solutions, dispersions or suspensions for example in an inert solvent, water or oil.

Component b) and a further additive can also be added to component a) in the form of a masterbatch (concentrate), which contains the component b), a further additive and a masterbatch polymer. The component b) and a further additive are incorporated into the masterbatch in a concentration of, for example, from 1% to 40% and preferably 2% to 20% by weight of the masterbatch. The masterbatch polymer content is the difference towards 100% by weight of the masterbatch. The masterbatch polymer must not be necessarily the same as polymer as component a) in case the latter one is a polymer.

A further embodiment of the invention relates to an additive composition, which comprises
b) a compound of formula I, and
c) a further additive selected from a group consisting of a phosphite or phosphonite, an acid scavenger, a phenolic antioxidant or an aminic antioxidant.

Preferred is a composition, wherein the weight ratio of component b) to component c) is from 10:1 to 1:30, in particular from 4:1 to 1:20, especially from 2:1 to 1:10.

Preferred is an additive composition, which comprises as component d) a second further additive.

Preferred is an additive composition, which comprises
b) a compound of formula I,
c) a further additive selected from a group consisting of a phosphite or phosphonite, an acid scavenger, a phenolic antioxidant or an aminic antioxidant, and
d) a second further additive selected from a group consisting of a phosphite or phosphonite, an acid scavenger, a phenolic antioxidant or an aminic antioxidant.

Preferred is a composition, wherein the weight ratio of component b) to component c) is from 10:1 to 1:30, in particular from 4:1 to 1:20, especially from 2:1 to 1:10, and wherein the weight ratio of component b) to component d) is from 10:1 to 1:30, in particular from 4:1 to 1:20, especially from 2:1 to 1:10.

A further embodiment of the invention relates to an article, which is made from a composition comprising
a) an organic material susceptible to oxidative, thermal or light-induced degradation, which is a polymer, and
b) a compound of formula I.

The composition can be advantageously used for the preparation of various shaped articles. Examples for such an article are:

I-1) Floating devices, marine applications, pontoons, buoys, plastic lumber for decks, piers, boats, kayaks, oars, and beach reinforcements.

I-2) Automotive applications, in particular bumpers, dashboards, battery, rear and front linings, moldings parts under the hood, hat shelf, trunk linings, interior linings, air bag covers, electronic moldings for fittings (lights), panes for dashboards, headlamp glass, instrument panel, exterior linings, upholstery, automotive lights, head lights, parking lights, rear lights, stop lights, interior and exterior trims; door panels; gas tank; glazing front side; rear windows; seat backing, exterior panels, wire insulation, profile extrusion for sealing, cladding, pillar covers, chassis parts, exhaust systems, fuel filter/filler, fuel pumps, fuel tank, body side mouldings, convertible tops, exterior mirrors, exterior trim, fasteners/fixings, front end module, glass, hinges, lock systems, luggage/roof racks, pressed/stamped parts, seals, side impact protection, sound deadener/insulator and sunroof.

I-3) Road traffic devices, in particular sign postings, posts for road marking, car accessories, warning triangles, medical cases, helmets, tires.

I-4) Devices for plane, railway, motor car (car, motorbike, trucks) including furnishings.

I-5) Devices for space applications, in particular rockets and satellites, e.g. reentry shields.

I-6) Devices for architecture and design, mining applications, acoustic quietized systems, street refuges, and shelters.

II-1) Appliances, cases and coverings in general and electric/electronic devices (personal computer, telephone, portable phone, printer, television-sets, audio and video devices), flower pots, satellite TV bowl, and panel devices.

II-2) Jacketing for other materials such as steel or textiles.

II-3) Devices for the electronic industry, in particular insulation for plugs, especially computer plugs, cases for electric and electronic parts, printed boards, and materials for electronic data storage such as chips, check cards or credit cards.

II-4) Electric appliances, in particular washing machines, tumblers, ovens (microwave oven), dish-washers, mixers, and irons.

II-5) Covers for lights (e.g. street-lights, lamp-shades).

II-6) Applications in wire and cable (semi-conductor, insulation and cable-jacketing).

II-7) Foils for condensers, refrigerators, heating devices, air conditioners, encapsulating of electronics, semi-conductors, coffee machines, and vacuum cleaners.

III-1) Technical articles such as cogwheel (gear), slide fittings, spacers, screws, bolts, handles, and knobs.

III-2) Rotor blades, ventilators and windmill vanes, solar devices, swimming pools, swimming pool covers, pool liners, pond liners, closets, wardrobes, dividing walls, slat walls, folding walls, roofs, shutters (e.g. roller shutters), fittings, connections between pipes, sleeves, and conveyor belts.

III-3) Sanitary articles, in particular shower cubicles, lavatory seats, covers, and sinks.

III-4) Hygienic articles, in particular diapers (babies, adult incontinence), feminine hygiene articles, shower curtains, brushes, mats, tubs, mobile toilets, tooth brushes, and bed pans.

III-5) Pipes (cross-linked or not) for water, waste water and chemicals, pipes for wire and cable protection, pipes for gas, oil and sewage, guttering, down pipes, and drainage systems.

III-6) Profiles of any geometry (window panes) and siding.

III-7) Glass substitutes, in particular extruded or co-extruded plates, glazing for buildings (monolithic, twin or multi-wall), aircraft, schools, extruded sheets, window film for architectural glazing, train, transportation, sanitary articles, and greenhouse.

III-8) Plates (walls, cutting board), extrusion-coating (photographic paper, tetrapack and pipe coating), silos, wood substitute, plastic lumber, wood composites, walls, surfaces, furniture, decorative foil, floor coverings (interior and exterior applications), flooring, duck boards, and tiles.

III-9) Intake and outlet manifolds.

III-10) Cement-, concrete-, composite-applications and covers, siding and cladding, hand rails, banisters, kitchen work tops, roofing, roofing sheets, tiles, and tarpaulins.

IV-1) Plates (walls and cutting board), trays, artificial grass, astroturf, artificial covering for stadium rings (athletics), artificial floor for stadium rings (athletics), and tapes.

IV-2) Woven fabrics continuous and staple, fibers (carpets/hygienic articles/geotextiles/monofilaments; filters; wipes/curtains (shades)/medical applications), bulk fibers (applications such as gown/protection clothes), nets, ropes, cables, strings, cords, threads, safety seat-belts, clothes, underwear, gloves; boots; rubber boots, intimate apparel, garments, swimwear, sportswear, umbrellas (parasol, sunshade), parachutes, paraglides, sails, "balloon-silk", camping articles, tents, airbeds, sun beds, bulk bags, and bags. Non-woven fabrics such as medical fabrics and related apparel, industrial apparel, outdoor fabrics, in-home furnishing and construction fabrics.

IV-3) Membranes, insulation, covers and seals for roofs, tunnels, dumps, ponds, dumps, walls roofing membranes, geomembranes, swimming pools, curtains (shades)/sunshields, awnings, canopies, wallpaper, food packing and wrapping (flexible and solid), medical packaging (flexible & solid), airbags/safety belts, arm- and head rests, carpets, centre console, dashboard, cockpits, door, overhead console module, door trim, headliners, interior lighting, interior mirrors, parcel shelf, rear luggage cover, seats, steering column, steering wheel, textiles, and trunk trim.

V) Films (packaging, dump, laminating, agriculture and horticulture, greenhouse, mulch, tunnel, silage), bale wrap, swimming pools, waste bags, wallpaper, stretch film, raffia, desalination film, batteries, and connectors.

VI-1) Food packing and wrapping (flexible and solid), bottles.

VI-2) Storage systems such as boxes (crates), luggage, chest, household boxes, pallets, shelves, tracks, screw boxes, packs, and cans.

VI-3) Cartridges, syringes, medical applications, containers for any transportation, waste baskets and waste bins, waste bags, bins, dust bins, bin liners, wheely bins, container in general, tanks for water/used water/chemistry/gas/oil/gasoline/diesel; tank liners, boxes, crates, battery cases, troughs, medical devices such as piston, ophthalmic applications, diagnostic devices, and packing for pharmaceuticals blister.

VII-1) Extrusion coating (photo paper, tetrapack, pipe coating), household articles of any kind (e.g. appliances, thermos bottle/clothes hanger), fastening systems such as plugs, wire and cable clamps, zippers, closures, locks, and snap-closures.

VII-2) Support devices, articles for the leisure time such as sports and fitness devices, gymnastics mats, ski-boots, inline-skates, skis, big foot, athletic surfaces (e.g. tennis grounds); screw tops, tops and stoppers for bottles, and cans.

VII-3) Furniture in general, foamed articles (cushions, impact absorbers), foams, sponges, dish clothes, mats, garden chairs, stadium seats, tables, couches, toys, building kits (boards/figures/balls), playhouses, slides, and play vehicles.

VII-4) Materials for optical and magnetic data storage.

VII-5) Kitchen ware (eating, drinking, cooking, storing).

VII-6) Boxes for CD's, cassettes and video tapes; DVD electronic articles, office supplies of any kind (ball-point pens, stamps and ink-pads, mouse, shelves, tracks), bottles of any volume and content (drinks, detergents, cosmetics including perfumes), and adhesive tapes.

VII-7) Footwear (shoes/shoe-soles), insoles, spats, adhesives, structural adhesives, food boxes (fruit, vegetables, meat, fish), synthetic paper, labels for bottles, couches, artificial joints (human), printing plates (flexographic), printed circuit boards, and display technologies.

VII-8) Devices of filled polymers (talc, chalk, china clay (kaolin), wollastonite, pigments, carbon black, $TiO_2$, mica, nanocomposites, dolomite, silicates, glass, asbestos).

Preferred is an article, which is a film, pipe, profile, bottle, tank, container or fiber.

Preferred is an article, which is moulded. In particular, the moulding is effected by injection, blow, compression, roto-moulding, slush-moulding or extrusion.

A further embodiment to the invention relates to the use of a compound of formula I, i.e. component b), for stabilizing an organic material susceptible to oxidative, thermal or light-induced degradation, i.e. component a), against degradation by oxidation, heat or light.

Preferred is the use of component b) for stabilizing a polyurethane foam against scorching.

Processing of a component a) is characterized as short-term exposure of the component a) to heat, for example to a temperature in the range of 150° C. to 340° C., during the time of processing of component a). The time of processing is short in comparison to for example the possible time of usage. Usage takes typically place at a temperature, for example 0° C. to 50° C., which is below the temperature during processing.

Preferred is the use of component b) for stabilizing a component a) against oxidative or thermal degradation during processing.

Compounds of formula I are partly new and partly known. Several synthetic routes to known compounds of formula I are described in literature.

A further embodiment of the invention relates to a compound of formula I

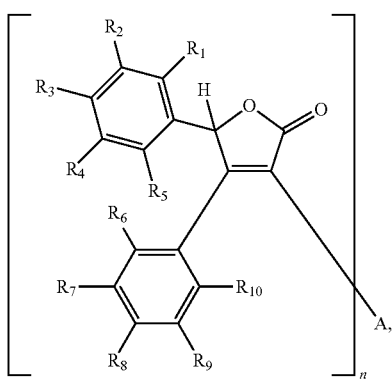

(I)

wherein
when n is 1
A is —C(=O)—OR'$_1$, —C(=O)—N(R'$_2$)(R'$_3$) or —SO$_2$-phenyl;
when n is 2
A is —C(=O)—O—Z$_1$—O—C(=O)—, —C(=O)—N(R"$_1$)—Z$_2$—N(R"$_2$)—C(=O)— or piperazine-N,N'-biscarbonyl;
when n is 3
A is C$_3$-C$_{12}$-alkane-tri-(oxycarbonyl), 3-ethyl-3-azapentane-1,5,2'-tri-(oxycarbonyl), 1,4,7-triazaheptane-1,4,7-tricarbonyl, 1,4,8-triazaoctane-1,4,8-tricarbonyl or 1,5,9-triazanonane-1,5,9-tricarbonyl;
when n is 4
A is C$_4$-C$_{16}$-alkane-tetra-(oxycarbonyl), 1,4,7,10-tetraazadecane-1,4,7,10-tetracarbonyl, 1,4,8,11-tetraazaundecane-1,4,8,11-tetracarbonyl or 1,5,8,12-tetraazadodecane-1,5,8,12-tetracarbonyl;
n is 1, 2, 3 or 4;
R$_1$, R$_2$, R$_3$, R$_4$, R$_5$, R$_6$, R$_7$, R$_8$, R$_9$ and R$_{10}$ are independently from each other H, C$_1$-C$_8$-alkyl, C$_4$-C$_8$-cycloalkyl, phenyl, C$_1$-C$_4$-alkoxy or halogen;
R'$_1$ is H, C$_1$-C$_{22}$-alkyl, C$_2$-C$_{18}$-alkenyl, C$_3$-C$_{12}$-alkine-yl, C$_4$-C$_8$-cycloalkyl, which is unsubstituted or substituted by one to three C$_1$-C$_4$-alkyl, C$_4$-C$_8$-cycloalkyl-C$_1$-C$_4$-alkyl, bicyclic or tricyclic C$_5$-C$_{20}$-alkyl, C$_6$-C$_{14}$-aryl-C$_1$-C$_4$-alkyl, C$_2$-C$_{12}$-alkyl, which is substituted by one or more hydroxyl groups, C$_4$-C$_{12}$-alkyl, which is interrupted by one or more oxygen atoms, C$_4$-C$_{18}$-alkyl, which is interrupted by one sulfur atom, 2,2,6,6-tetramethylpiperidine-4-yl, 1-(C$_1$-C$_8$-alkyl)-2,2,6,6-tetramethylpiperidine-4-yl or 1-(C$_1$-C$_8$-alkoxy)-2,2,6,6-tetramethylpiperidine-4-yl;
R'$_2$ and R'$_3$ are independently from each other H, C$_1$-C$_{22}$-alkyl, C$_2$-C$_{18}$-alkenyl, C$_4$-C$_8$-cycloalkyl, which is unsubstituted or substituted by one to three C$_1$-C$_4$-alkyl, C$_6$-C$_{10}$-aryl, C$_4$-C$_8$-cycloalkyl-C$_1$-C$_4$-alkyl, C$_6$-C$_{14}$-aryl-C$_1$-C$_4$-alkyl, C$_2$-C$_6$-alkyl, which is substituted by a hydroxyl group, 2,2,6,6-tetramethylpiperidine-4-yl, 1-(C$_1$-C$_8$-alkyl)-2,2,6,6-tetramethylpiperidine-4-yl or 1-(C$_1$-C$_8$-alkoxy)-2,2,6,6-tetramethylpiperidine-4-yl, or R'$_2$ and R'$_3$ form together with the nitrogen atom to which they are attached a 5-, 6- or 7-membered saturated heterocycle;
R"$_1$ and R"$_2$ are independently from each other H, C$_1$-C$_{22}$-alkyl, C$_2$-C$_{18}$-alkenyl, C$_4$-C$_8$-cycloalkyl, which is unsubstituted or substituted by one to three C$_1$-C$_4$-alkyl, C$_4$-C$_8$-cycloalkyl-C$_1$-C$_4$-alkyl, C$_6$-C$_{14}$-aryl-C$_1$-C$_4$-alkyl;
Z$_1$ is C$_2$-C$_{12}$-alkylene, C$_4$-C$_8$-cycloalkylene, C$_4$-C$_8$-cycloalkane-bis-(C$_1$-C$_4$-alkylene), C$_6$-C$_4$-arene-bis-(C$_1$-C$_4$-alkylene), C$_3$-C$_6$-alkylene, which is substituted by one or more hydroxyl groups, C$_4$-C$_{12}$-alkylene, which is interrupted by one or more oxygen atoms, hexahydro-furo[3,2-b]furane-3,6-diyl, C$_4$-C$_8$-alkylene, which is interrupted by a sulfur atom, 3-(C$_1$-C$_8$-alkyl)-3-azapentane-1,5-diyl, 4-(C$_1$-C$_8$-alkyl)-4-azaheptane-1,7-diyl or 1-ethyl-2,2,6,6-tetramethylpiperidine-4,2'-diyl; and
Z$_2$ is C$_2$-C$_{12}$-alkylene, C$_4$-C$_8$-cycloalkylene, C$_6$-C$_{14}$-arylene, C$_4$-C$_8$-cycloalkane-bis(C$_1$-C$_4$-alkylene), C$_6$-C$_{14}$-arene-bis-(C$_1$-C$_4$-alkylene), C$_4$-C$_{12}$-alkylene, which is interrupted by one or more oxygen atoms, 3-(C$_1$-C$_8$-alkyl)-3-azapentane-1,5-diyl or 4-(C$_1$-C$_8$-alkyl)-4-azaheptane-1,7-diyl.

Preferred is a compound of formula I, wherein
when n is 1
A is —C(=O)—OR'$_1$ or —C(=O)—N(R'$_2$)(R'$_3$);
when n is 2
A is —C(=O)—O—Z$_1$—O—C(=O)—, —O(=O)—N(R"$_1$)—Z$_2$—N(R"$_2$)—O(=O)— or piperazine-N,N'-biscarbonyl;
when n is 3
A is C$_3$-C$_{12}$-alkane-tri-(oxycarbonyl);
when n is 4
A is C$_4$-C$_{16}$-alkane-tetra-(oxycarbonyl);
n is 1, 2, 3 or 4;
R$_1$, R$_2$, R$_3$, R$_4$, R$_5$, R$_6$, R$_7$, R$_8$, R$_9$ and R$_{10}$ are independently from each other H, C$_1$-C$_8$-alkyl, C$_4$-C$_8$-cycloalkyl, phenyl, C$_1$-C$_4$-alkoxy or halogen;
R'$_1$ is H, C$_1$-C$_{22}$-alkyl, C$_2$-C$_{18}$-alkenyl, C$_3$-C$_{12}$-alkine-yl, C$_4$-C$_8$-cycloalkyl, which is unsubstituted or substituted by one to three C$_1$-C$_4$-alkyl, C$_4$-C$_8$-cycloalkyl-C$_1$-C$_4$-alkyl, bicyclic or tricyclic C$_5$-C$_{20}$-alkyl, C$_6$-C$_{14}$-aryl-C$_1$-C$_4$-alkyl, C$_2$-C$_{12}$-alkyl, which is substituted by one or more hydroxyl groups, C$_4$-C$_{12}$-alkyl, which is interrupted by one or more oxygen atoms, C$_4$-C$_{18}$-alkyl, which is interrupted by one sulfur atom, 2,2,6,6-tetramethylpiperidine-4-yl, 1-(C$_1$-C$_8$-alkyl)-2,2,6,6-tetramethylpiperidine-4-yl or 1-(C$_1$-C$_8$-alkoxy)-2,2,6,6-tetramethylpiperidine-4-yl;
R'$_2$ and R'$_3$ are independently from each other H, C$_1$-C$_{22}$-alkyl, C$_2$-C$_{18}$-alkenyl, C$_4$-C$_8$-cycloalkyl, which is unsubstituted or substituted by one to three C$_1$-C$_4$-alkyl, C$_6$-C$_{10}$-aryl, C$_4$-C$_8$-cycloalkyl-C$_1$-C$_4$-alkyl, C$_6$-C$_{14}$-aryl-C$_1$-C$_4$-alkyl, C$_2$-C$_6$-alkyl, which is substituted by a hydroxyl group, 2,2,6,6-tetramethylpiperidine-4-yl, 1-(C$_1$-C$_8$-alkyl)-2,2,6,6-tetramethylpiperidine-4-yl or 1-(C$_1$-C$_8$-alkoxy)-2,2,6,6-tetramethylpiperidine-4-yl, or R'$_2$ and R'$_3$ form together with the nitrogen atom to which they are attached a 5-, 6- or 7-membered saturated heterocycle;
R"$_1$ and R"$_2$ are independently from each other H, C$_1$-C$_{22}$-alkyl, C$_2$-C$_{18}$-alkenyl, C$_4$-C$_8$-cycloalkyl, which is unsubstituted or substituted by one to three C$_1$-C$_4$-alkyl, C$_4$-C$_8$-cycloalkyl-C$_1$-C$_4$-alkyl, C$_6$-C$_{14}$-aryl-C$_1$-C$_4$-alkyl;
Z$_1$ is C$_2$-C$_{12}$-alkylene, C$_4$-C$_8$-cycloalkylene, C$_4$-C$_8$-cycloalkane-bis-(C$_1$-C$_4$-alkylene), C$_6$-C$_{14}$-arene-bis-(C$_1$-C$_4$- alkylene), $C_3$-$C_6$-alkylene, which is substituted by one or more hydroxyl groups, $C_4$-$C_{12}$-alkylene, which is interrupted by one or more oxygen atoms, hexahydro-furo[3,2-b]furane-3,6-diyl, $C_4$-$C_8$-alkylene, which is interrupted by a sulfur atom, 3-($C_1$-$C_8$-alkyl)-3-azapentane-1,5-diyl, 4-($C_1$-$C_8$-alkyl)-4-azaheptane-1,7-diyl or 1-ethyl-2,2,6,6-tetramethylpiperidine-4,2'-diyl; and $Z_2$ is $C_2$-$C_{12}$-alkylene, $C_4$-$C_8$-cycloalkylene, $C_6$-$C_{14}$-arylene, $C_4$-$C_8$-cycloalkane-bis($C_1$-$C_4$-alkylene), $C_6$-$C_{14}$-arene-bis-($C_1$-$C_4$-alkylene), $C_4$-$C_{12}$-alkylene, which is interrupted by one or more oxygen atoms, 3-($C_1$-$C_8$-alkyl)-3-azapentane-1,5-diyl or 4-($C_1$-$C_8$-alkyl)-4-azaheptane-1,7-diyl.

A further embodiment of the invention relates to a synthesis method for a compound of formula I

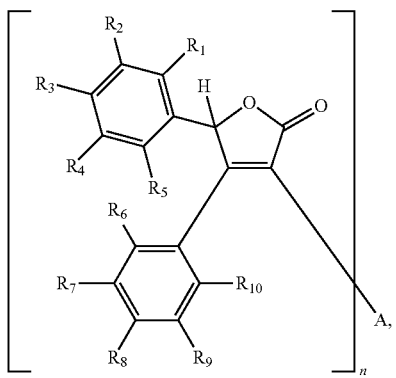

(I)

wherein n is 1;

A is —C(=O)—OR'$_1$, —C(=O)—N(R'$_2$)(R'$_3$);

$R_1$, $R_2$, $R_3$, $R_4$, $R_5$, $R_6$, $R_7$, $R_8$, $R_9$ and $R_{10}$ are independently from each other H, $C_1$-$C_8$-alkyl, $C_4$-$C_8$-cycloalkyl, phenyl, $C_1$-$C_4$-alkoxy or halogen;

R'$_1$ is H, $C_1$-$C_{22}$-alkyl, $C_2$-$C_{18}$-alkenyl, $C_3$-$C_{12}$-alkine-yl, $C_4$-$C_8$-cycloalkyl, which is unsubstituted or substituted by one to three $C_1$-$C_4$-alkyl, $C_4$-$C_8$-cycloalkyl-$C_1$-$C_4$-alkyl, bicyclic or tricyclic $C_5$-$C_{20}$-alkyl, $C_6$-$C_{14}$-aryl-$C_1$-$C_4$-alkyl, $C_2$-$C_{12}$-alkyl, which is substituted by one or more hydroxyl groups, $C_4$-$C_{12}$-alkyl, which is interrupted by one or more oxygen atoms, $C_4$-$C_{18}$-alkyl, which is interrupted by one sulfur atom, 2,2,6,6-tetramethylpiperidine-4-yl, 1-($C_1$-$C_8$-alkyl)-2,2,6,6-tetramethylpiperidine-4-yl or 1-($C_1$-$C_8$-alkoxy)-2,2,6,6-tetramethylpiperidine-4-yl;

R'$_2$ and R'$_3$ are independently from each other H, $C_1$-$C_{22}$-alkyl, $C_2$-$C_{18}$-alkenyl, $C_4$-$C_8$-cycloalkyl, which is unsubstituted or substituted by one to three $C_1$-$C_4$-alkyl, $C_6$-$C_{10}$-aryl, $C_4$-$C_8$-cycloalkyl-$C_1$-$C_4$-alkyl, $C_6$-$C_{14}$-aryl-$C_1$-$C_4$-alkyl, $C_2$-$C_8$-alkyl, which is substituted by one hydroxyl group, 2,2,6,6-tetramethylpiperidine-4-yl, 1-($C_1$-$C_8$-alkyl)-2,2,6,6-tetramethylpiperidin-4-yl or 1-($C_1$-$C_8$-alkoxy)-2,2,6,6-tetramethylpiperidine-4-yl, or R'$_2$ and R'$_3$ form together with the nitrogen atom to which they are attached a 5-, 6- or 7-membered saturated heterocycle;

which comprises the step of reacting a compound of formula II

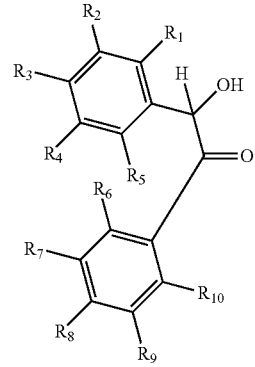

(II)

wherein $R_1$, $R_2$, $R_3$, $R_4$, $R_5$, $R_6$, $R_7$, $R_8$, $R_9$ and $R_{10}$ have the meaning as indicated above; with a compound of formula III

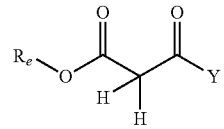

(III)

wherein $R_e$ is $C_1$-$C_8$-alkyl;

Y is OR', or N(R'$_2$)(R'$_3$); and

R'$_1$, R'$_2$ and R'$_3$ have the meaning as indicated above; in the presence of an organic or inorganic base and a solvent.

Preferably, $R_e$ is $C_1$-$C_4$-alkyl, in particular methyl or ethyl.

Preferably, the organic base is sodium methanolate or sodium ethanolate.

Preferably, the solvent is methanol or ethanol, in particular methanol.

Preferably, the temperature during the synthesis is in the range of 0° C. to 240° C.

A further embodiment of the invention relates to a synthesis method for a compound of formula I

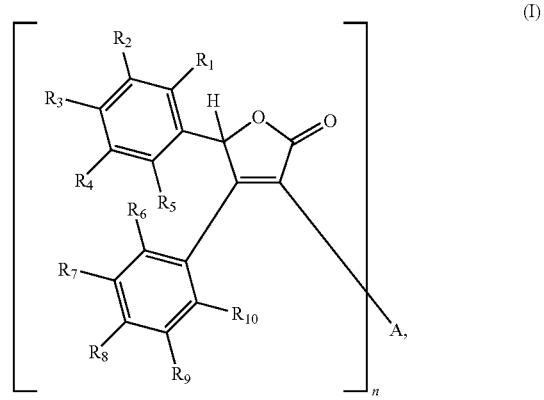

(I)

wherein n is 2;

A is —C(=O)—O—Z$_1$—O—C(=O)—;

$R_1, R_2, R_3, R_4, R_5, R_6, R_7, R_8, R_9$ and $R_{10}$ are independently from each other H, $C_1$-$C_8$-alkyl, $C_4$-$C_8$-cycloalkyl, phenyl, $C_1$-$C_4$-alkoxy or halogen; and $Z_1$ is $C_2$-$C_{12}$-alkylene, $C_4$-$C_8$-cycloalkylene, $C_4$-$C_8$-cycloalkane-bis-($C_1$-$C_4$-alkylene), $C_6$-$C_{14}$-arene-bis-($C_1$-$C_4$-alkylene), $C_3$-$C_6$-alkylene, which is substituted by one or more hydroxyl groups, $C_4$-$C_{12}$-alkylene, which is interrupted by one or more oxygen atoms, hexahydro-furo[3,2-b]furane-3,6-diyl, $C_4$-$C_8$-alkylene, which is interrupted by a sulfur atom, 3-($C_1$-$C_8$-alkyl)-3-azapentane-1,5-diyl, 4-($C_1$-$C_8$-alkyl)-4-azaheptane-1,7-diyl or 1-ethyl-2,2,6,6-tetramethylpiperidine-4,2'-diyl;

which comprises the step of reacting a compound of formula Ia

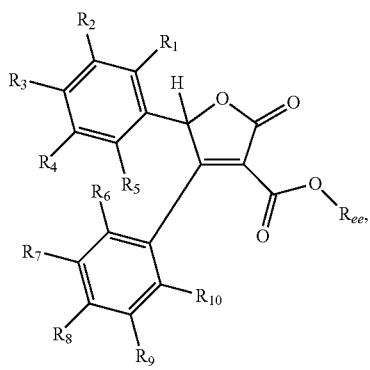

(Ia)

wherein $R_{ee}$ is $C_1$-$C_8$-alkyl; and $R_1, R_2, R_3, R_4, R_5, R_6, R_7, R_8, R_9$ and $R_{10}$ have the meaning as indicated above;

with a compound of formula V

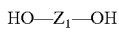 HO—$Z_1$—OH (V)

wherein $Z_1$ has the meaning as indicated above;

in the presence of a solvent.

Preferably, the temperature during the synthesis is in the range of 70° C. to 240° C.

Preferably, $R_e$ is $C_1$-$C_4$-alkyl, in particular methyl or ethyl.

Preferably, the solvent has a boiling point above the boiling point of $R_{ee}$—OH. Preferably, the solvent is free of a hydroxyl group. For example, the solvent is toluene, xylene or dichlorobenzene.

Preferably, the synthesis is conducted under vacuum.

Preferably, a transesterification catalyst is added.

The following examples illustrate further the invention without limiting it.

EXAMPLE 1

2-Oxo-4,5-diphenyl-2,5-dihydro-furan-3-carboxylic acid methyl ester (201)

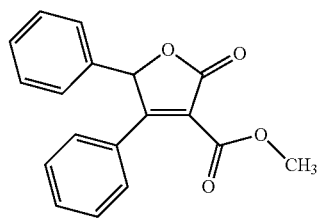 [SMILES: COC(=O)C1=C(c2ccccc2)C(c2ccccc2)OC1=O]

45 g benzoin (=2-hydroxy-1,2-bis-phenyl-ethanone; 212 mmol) and 70 g dimethyl malonate (530 mmol) are dissolved under reflux in 75 mL methanol. 22.9 g sodium methoxide (424 mmol) is dissolved in 1250 mL methanol and added. The mixture is stirred at 40° for 1 h and then acidified with diluted aqueous hydrochloric acid to pH 3-4. The precipitate is filtered off, washed with water and afterwards with methanol and dried in vacuo. 50.8 g of compound (201) are obtained (81%); mp. 113-115°.

EXAMPLE 2

4,5-Bis-(4-methoxy-phenyl)-2-oxo-2,5-dihydro-furan-3-carboxylic acid methyl ester (202)

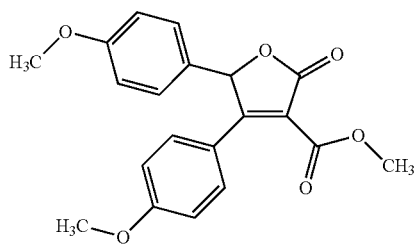

10 g anisoin (=2-hydroxy-1,2-bis-(4-methoxy-phenyl)-ethanone; 36.7 mmol) and 12.13 g dimethyl malonate (91.8 mmol) are dissolved in 70 mL methanol under reflux. 1.68 g sodium (73.4 mmol) is dissolved in 70 mL methanol and added. The mixture is refluxed for 18 h, then cooled to 25° and acidified with diluted aqueous hydrochloric acid. The resulting mixture is extracted with ethyl acetate/toluene. The organic phases are washed with water, dried over magnesium sulfate, and evaporated to dryness. Recrystallization from methanol yields 5.61 g of compound (202) (41%); mp. 107-109°.

EXAMPLE 3

2-Oxo-4,5-diphenyl-2,5-dihydro-furan-3-carboxylic acid amide (203)

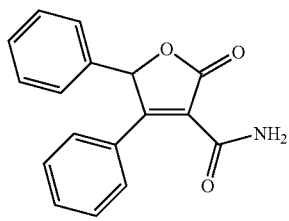 [SMILES: NC(=O)C1=C(c2ccccc2)C(c2ccccc2)OC1=O]

10 g benzoin (47 mmol) and 11 g methyl malonamate (94 mmol) are dissolved in 100 mL methanol at reflux. 5.07 g sodium methoxide (94 mmol) is dissolved in 40 mL methanol and added. The mixture is refluxed for 1 h. The resulting suspension is acidified at 25° with diluted aqueous hydrochloric acid to pH 3-4 and the precipitate is filtered off, dried and recrystallized from toluene. 10.1 g of compound (203) is obtained (77%); mp. 125-127°.

EXAMPLE 4

2-Oxo-4,5-diphenyl-2,5-dihydro-furan-3-carboxylic acid octylamide (204)

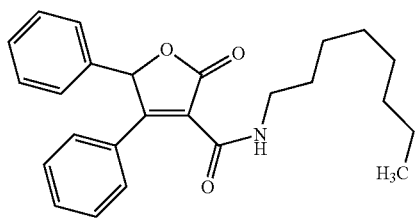 [SMILES: CCCCCCCCNC(=O)C1=C(c2ccccc2)C(c2ccccc2)OC1=O]

1 g benzoin (4.7 mmol) and 1.6 g of compound (401) (7 mmol) are dissolved in 5 mL methanol. 0.63 g of sodium methoxide (9.4 mmol) in 5 mL methanol is added and the mixture is refluxed for 2 h. The mixture is acidified with diluted aqueous hydrochloric acid to pH 3-4 and extracted twice with ethyl acetate. The organic phases are washed with water, dried over sodium sulfate and evaporated to dryness. 1.25 g of compound (204) is obtained as vicous oil (68%).

EXAMPLE 5

2-Oxo-4,5-diphenyl-2,5-dihydro-furan-3-carboxylic acid cyclohexylamide (205)

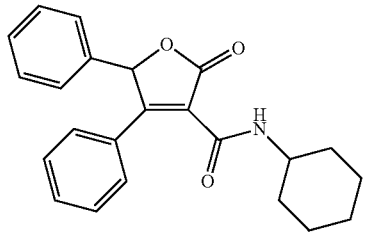 [SMILES: O=C(NC1CCCCC1)C1=C(c2ccccc2)C(c2ccccc2)OC1=O]

In analogy to example 4, benzoin and compound (402) are reacted and compound (205) is obtained (49%); mp. 151-153° C.

EXAMPLE 6

2-Oxo-4,5-diphenyl-2,5-dihydro-furan-3-carboxylic acid (1,1,3,3-tetramethyl-butyl)-amide (206)

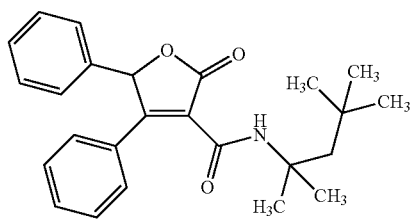 [SMILES: CC(C)(C)CC(C)(C)NC(=O)C1=C(c2ccccc2)C(c2ccccc2)OC1=O]

In analogy to example 4, benzoin and compound (403) are reacted and compound (206) is obtained (64%); mp. 110-111° C.

EXAMPLE 7

2-Oxo-4,5-diphenyl-2,5-dihydro-furan-3-carboxylic acid benzylamide (207)

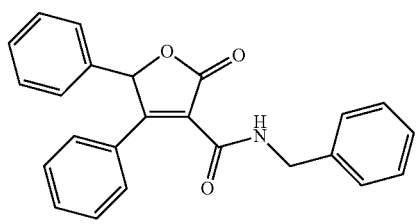 [SMILES: O=C(NCc1ccccc1)C1=C(c2ccccc2)C(c2ccccc2)OC1=O]

In analogy to example 4, benzoin and compound (404) are reacted and compound (207) is obtained (54%); mp. 173-175° C.

EXAMPLE 8

2-Oxo-4,5-diphenyl-2,5-dihydro-furan-3-carboxylic acid (2,2,6,6-tetramethyl-1-propoxy-piperidin-4-yl)-amide (208)

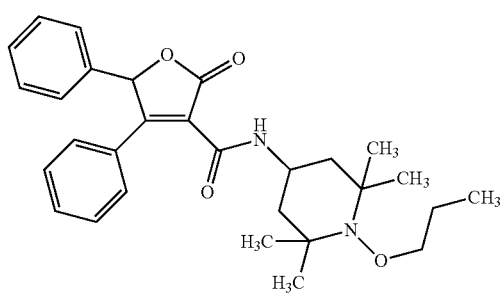 [SMILES: CCCON1C(C)(C)CC(NC(=O)C2=C(c3ccccc3)C(c3ccccc3)OC2=O)CC1(C)C]

In analogy to example 4, benzoin and compound (405) are reacted and compound (208) is obtained (99%) as waxy solid; mp. 79-85° C.

EXAMPLE 9

2-Oxo-4,5-diphenyl-2,5-dihydro-furan-3-carboxylic acid dibutylamide (209)

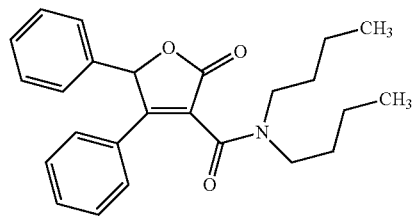 [SMILES: CCCCN(CCCC)C(=O)C1=C(c2ccccc2)C(c2ccccc2)OC1=O]

7.4 g benzoin (35 mmol) and 12 g of compound (406) (52 mmol) are dissolved in 80 mL methanol at reflux. 3.78 g sodium methoxide (70 mmol) is dissolved in 40 mL methanol and added. The reaction mixture is refluxed for 2.5 h. Then, the mixture is acidified with diluted aqueous hydrochloric acid to pH 3-4 and extracted with diethyl ether. The organic phase is separated, washed with water, dried over sodium sulfate, and evaporated in vacuo. 13.6 g of compound (209) is obtained (99%) as a slightly yellow liquid; MS (liquid chromatography/mass spectroscopy atmospheric pressure chemical ionisation (positive mode) (=LC/MS APCI (pos. mode)): 392 ([MH]$^+$).

EXAMPLE 10

3-(Morpholine-4-carbonyl)-4,5-diphenyl-5H-furan-2-one (210)

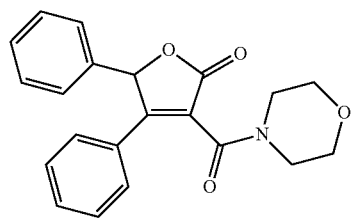 [SMILES: O=C1OC(c2ccccc2)C(c2ccccc2)=C1C(=O)N1CCOCC1]

In analogy to example 9, benzoin and compound (407) are reacted and compound (210) is obtained (92%); mp. 204-206° C.

EXAMPLE 11

2-Oxo-4,5-diphenyl-2,5-dihydro-furan-3-carboxylic acid phenylamide (211)

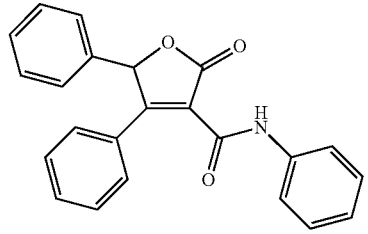 [SMILES: O=C(Nc1ccccc1)C1=C(c2ccccc2)C(c2ccccc2)OC1=O]

In analogy to example 9, benzoin and compound (408) are reacted and compound (211) is obtained (58%); mp. 148-150° C.

EXAMPLE 12

2-Oxo-4,5-diphenyl-2,5-dihydro-furan-3-carboxylic acid ethyl ester (212)

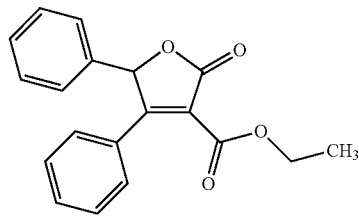 [SMILES: CCOC(=O)C1=C(c2ccccc2)C(c2ccccc2)OC1=O]

5 g of compound (201) (17 mmol) is dissolved in 50 mL ethanol and heated to reflux with a oilbath temperature of 100° C. A mixture of ethanol and methanol is distilled off. Ethanol is replaced regularly under these distillation conditions. After 8 h of distilling, the turnover is complete and the solution is evaporated in vacuo. 4.77 g of compound (212) is obtained (91%) as a viscous oil.

EXAMPLE 13

2-Oxo-4,5-diphenyl-2,5-dihydro-furan-3-carboxylic acid propyl ester (213)

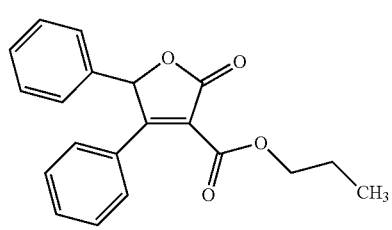 [SMILES: CCCOC(=O)C1=C(c2ccccc2)C(c2ccccc2)OC1=O]

In analogy to example 12, compound (201) and 1-propanol are reacted and compound (213) is obtained (98%) as a liquid.

EXAMPLE 14

2-Oxo-4,5-diphenyl-2,5-dihydro-furan-3-carboxylic acid pentyl ester (214)

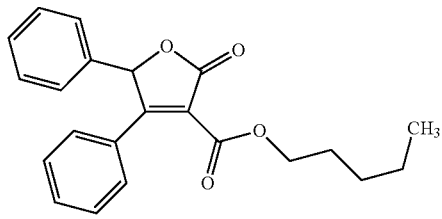 [SMILES: CCCCCOC(=O)C1=C(c2ccccc2)C(c2ccccc2)OC1=O]

In analogy to example 12, compound (201) and 1-pentanol are reacted and compound (214) is obtained (83%) as liquid.

EXAMPLE 15

2-Oxo-4,5-diphenyl-2,5-dihydro-furan-3-carboxylic acid 1-methoxy-2,2,6,6-tetramethyl-piperidin-4-yl ester (215)

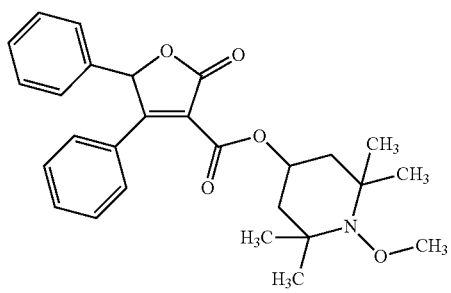 [SMILES: CON1C(C)(C)CC(OC(=O)C2=C(c3ccccc3)C(c3ccccc3)OC2=O)CC1(C)C]

In analogy to example 12 and with tetralin employed as co-solvent, compound (201) and 1-methoxy-2,2,6,6-tetramethyl-piperidin-4-ol are reacted and compound (215) is obtained (37%); mp. 143-146° C.

EXAMPLE 16

2-Oxo-4,5-diphenyl-2,5-dihydro-furan-3-carboxylic acid cyclohexyl ester (216)

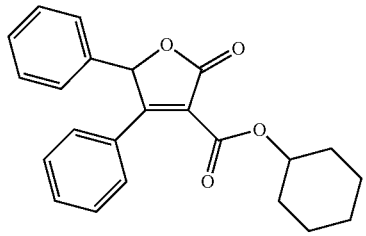 [SMILES: O=C(OC1CCCCC1)C1=C(c2ccccc2)C(c2ccccc2)OC1=O]

In analogy to example 12, compound (201) and cyclohexanol are reacted and compound (216) is obtained (82%); mp. 139-142° C.

EXAMPLE 17

2-Oxo-4,5-diphenyl-2,5-dihydro-furan-3-carboxylic acid benzyl ester (217)

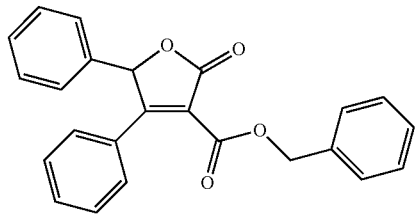 [SMILES: O=C(OCc1ccccc1)C1=C(c2ccccc2)C(c2ccccc2)OC1=O]

In analogy to example 12, compound (201) and benzyl alcohol are reacted and compound (217) is obtained (73%); mp. 111-114° C.

EXAMPLE 18

2-Oxo-4,5-diphenyl-2,5-dihydro-furan-3-carboxylic acid isopropyl ester (218)

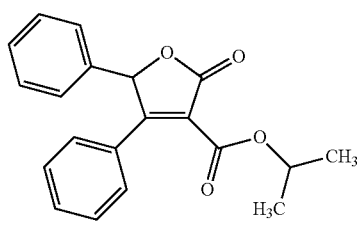 [SMILES: CC(C)OC(=O)C1=C(c2ccccc2)C(c2ccccc2)OC1=O]

In analogy to example 12, compound (201) and isopropanol are reacted and compound (218) is obtained (85%); mp. 120-122° C.

EXAMPLE 19

2-Oxo-4,5-diphenyl-2,5-dihydro-furan-3-carboxylic acid tert-butyl ester (219)

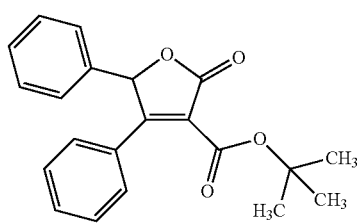 [SMILES: CC(C)(C)OC(=O)C1=C(c2ccccc2)C(c2ccccc2)OC1=O]

In analogy to example 12, compound (201) and 2-methyl-2-propanol are reacted and compound (219) is obtained (75%); mp. 109-111° C.

EXAMPLE 20

Bis-(2-oxo-4,5-diphenyl-2,5-dihydro-furan-3-carboxylic acid) cyclohexane-1,4-diyl diester (220)

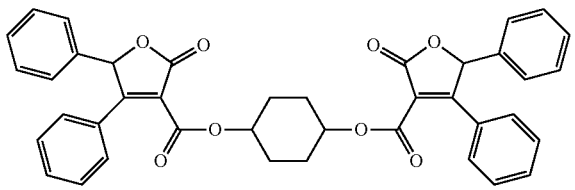 [SMILES: O=C(OC1CCC(OC(=O)C2=C(c3ccccc3)C(c3ccccc3)OC2=O)CC1)C1=C(c2ccccc2)C(c2ccccc2)OC1=O]

50 g of compound (201) (170 mmol) is melted at 140°. 10 g cyclohexan-1,4-diol (mixture of cis- and trans-isomer, 87 mmol) is added and followed by addition of 20 mL o-dichlorobenzene. The resulting methanol is distilled off at oil bath temperature of 190°. After 6 h the mixture is cooled to room temperature and 50 mL toluene is added. The precipitate is filtered off, washed with toluene, then hexane, and dried in vacuo. 18.61 g of compound (220) as a mixture of isomers is obtained (33%); mp. 237-240° C.

EXAMPLE 21

2-Oxo-4,5-diphenyl-2,5-dihydro-furan-3-carboxylic acid (221)

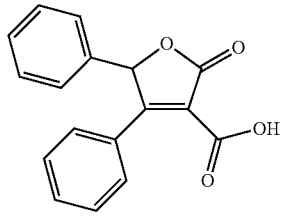 [SMILES: O=C(O)C1=C(c2ccccc2)C(c2ccccc2)OC1=O]

15 g of compound (219) (44 mmol) is stirred into 100 mL of sulfuric acid (96%) at 25°. After 1 h, the solution is added dropwise to a mixture of ice-water and dichloromethane under stirring. The organic phases are washed with water, then brine, dried over sodium sulfate, and evaporated to dryness. Recrystallization from chloroform yields 5.77 g of compound (221) (46%); mp. 116-117°.

EXAMPLE 22

2-Oxo-4,5-diphenyl-2,5-dihydro-furan-3-carbonitrile (222)

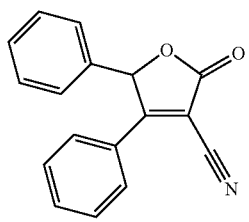 [SMILES: N#CC1=C(c2ccccc2)C(c2ccccc2)OC1=O]

Compound (222) is prepared according to J. A. McRae and A. L. Kuehner, Journal of the American Chemical Society, 1930, 52, 3377-3382.

EXAMPLE 23

4,5-Bis-(4-methoxy-phenyl)-2-oxo-2,5-dihydro-furan-3-carbonitrile (223)

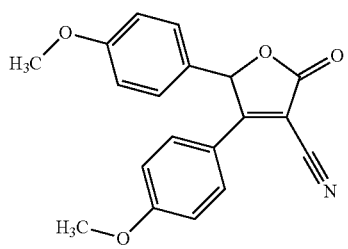 [SMILES: COc1ccc(C2=C(C#N)C(=O)OC2c2ccc(OC)cc2)cc1]

Compound (223) is prepared in analogy to compound (222).

EXAMPLE 24

4,5-Diphenyl-5H-furan-2-one (224)

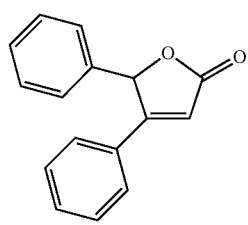 [SMILES: O=C1C=C(c2ccccc2)C(c2ccccc2)O1]

Compound (224) is a known compound.

10 g benzoin (47 mmol) and 37.6 g dimethyl malonate (235 mmol) are heated to 170° C. for 2 h. After cooling to room temperature, the reaction mass is triturated with hexane, the precipitate is filtered off and dried in vacuum. 6.7 g of compound (224) is obtained (60.5%) as white crystals; mp. 147149° C.

EXAMPLE 25

3-Benzenesulfonyl-4,5-diphenyl-5H-furan-2-one (225)

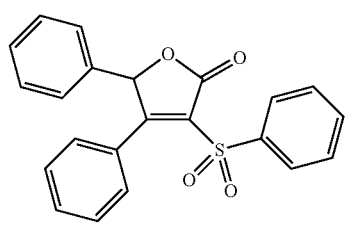 [SMILES: O=C1OC(c2ccccc2)C(c2ccccc2)=C1S(=O)(=O)c1ccccc1]

In analogy to example 2, 2.92 g benzoin (13 mmol) and 5.0 g phenylsulfonyl acetic acid methyl ester (20 mmol) are reacted. 4.02 g of compound (225) is obtained (76%) as yellow oil; MS (LC/MS APCI (pos. mode)): 377 ([MH]⁺).

EXAMPLE 26

3,4,5-Triphenyl-5H-furan-2-one (226)

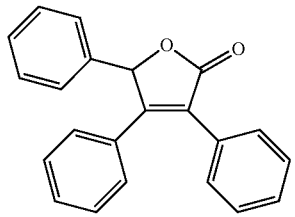 [SMILES: O=C1OC(c2ccccc2)C(c2ccccc2)=C1c1ccccc1]

Compound (226) is a known compound.

40 g benzoin (=2-hydroxy-1,2-bis-phenyl-ethanone; 188 mmol) and 84.9 g methylphenyl acetate (565 mmol) are dissolved under reflux in 200 mL methanol. 30.5 g sodium methoxide (565 mmol) is dissolved in 100 mL methanol and added. The mixture is stirred at 65° C. for 15 h and then acidified with diluted aqueous hydrochloric acid to pH 3-4. The precipitate is filtered off, washed with water and afterwards with methanol and dried in vacuo. 44.4 g of compound (226) are obtained, which are recrystallized from ethyl acetate/hexane to obtain 29.9 g (51%) of compound (226) as white crystals; mp. 120-122° C., MS (LC/MS APCI (pos. mode)): 313 ([MH]⁺).

EXAMPLE 27

N-Octyl-malonamic acid methyl ester (401)

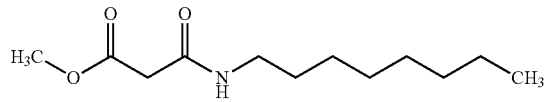 [SMILES: CCCCCCCCNC(=O)CC(=O)OC]

13.2 g dimethyl malonate (100 mmol) and 6.45 g octylamine (50 mmol) are heated to 125° C. and resulting methanol is distilled off. After 2.5 h at 125°, the reaction mixture is cooled to room temperature, the side product (bisamide) is precipitated with methanol and removed by filtration. The filtrate is concentrated in vacuo. 7.41 g of compound (401) is obtained (65%) as a liquid; pure by ¹H-NMR.

EXAMPLE 28

N-Cyclohexyl-malonamic acid methyl ester (402)

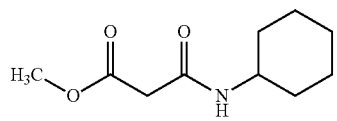

In analogy to example 27, compound (402) is obtained (64%); mp. 77-78° C.

EXAMPLE 29

N-(1,1,3,3-Tetramethyl-butyl)-malonamic acid methyl ester (403)

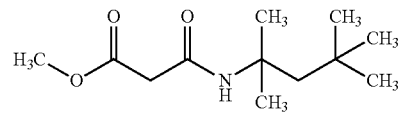 [SMILES: COC(=O)CC(=O)NC(C)(C)CC(C)(C)C]

In analogy to example 27, compound (403) is obtained (97%); mp. 74-75° C.

EXAMPLE 30

N-Benzyl-malonamic acid methyl ester (404)

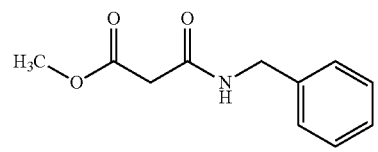

In analogy to example 27, compound (404) is obtained (63%); mp. 51-54° C.

EXAMPLE 31

N-(2,2,6,6-Tetramethyl-1-propoxy-piperidin-4-yl)-malonamic acid methyl ester (405)

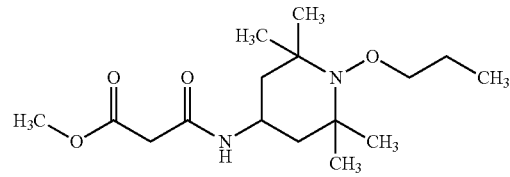 [SMILES: CCCON1C(C)(C)CC(NC(=O)CC(=O)OC)CC1(C)C]

In analogy to example 27, compound (405) is obtained (55%) as semi-crystalline/waxy material.

EXAMPLE 32

N,N-Dibutyl-malonamic acid methyl ester (406)

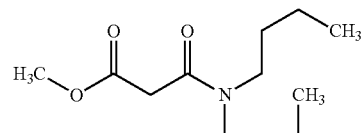

10 g methyl malonyl monochloride (=chlorocarbonyl-acetic acid methyl ester; 73 mmol) and 20.8 g dibutylamine (161 mmol, in excess) are reacted in diethylether at 0° C. Compound (406) is obtained (78%) as yellow, viscous oil.

EXAMPLE 33

3-Morpholin-4-yl-3-oxo-propionic acid methyl ester (407)

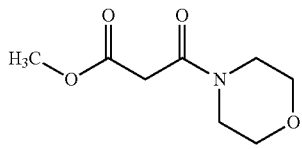

In analogy to example 32, compound (407) is obtained (69.5%) as orange, viscous oil.

EXAMPLE 34

N-Phenyl-malonamic acid methyl ester (408)

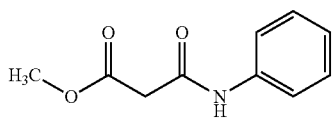

In analogy to example 32, compound (408) is obtained (89.8%) as white crystals.

EXAMPLE 35

Stabilization of Polyol

The oxidation resistance of polyol is determined by differential scanning calorimetry (DSC). A sample is heated starting at 50° C. with a heating rate of 5° C./min under oxygen until 200° C. are reached. The appearance of an exothermic peak indicates the beginning of a thermo-oxidative reaction. The temperature at the onset of the exothermic peak is noted. A better stabilized sample is characterized by a higher temperature for the onset.

100 parts of Lupranol 2084 (RTM BASF; polyol) are admixed with 0.45 parts of a stabilizer composition, which consists of Irganox 1135 (RTM BASF; 0.32 parts based on 100 parts of polyol), Irganox 5057 (RTM BASF; 0.10 parts based on 100 parts of polyol) and a compound of formula I according to the invention (0.03 parts based on 100 parts of polyol). In comparative example 35a), no stabilizer composition is added.

Lupranol 2084 (RTM BASF) is a trifunctional polyether polyol, which contains predominantly secondary hydroxyl groups and which possess a hydroxyl number 48 mg KOH/g, a water content less than 0.1% and an acid number less than 0.06 mg KOH/g.

Irganox 1135 (RTM BASF) is a phenolic antioxidant and contains 3-(3,5-di-tert-butyl-4-hydroxy-phenyl)-propionic acid iso-octyl ester as depicted:

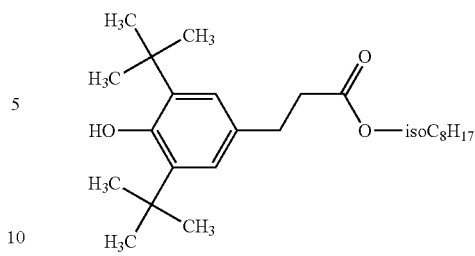

Irganox 5057 (RTM BASF) is an aminic antioxidant and is a technical mixture obtained by the reaction of diphenylamine with diisobutylene, comprising
α) diphenylamine;
β) 4-tert-butyldiphenylamine;
γ) compounds of the group
  i) 4-tert-octyldiphenylamine,
  ii) 4,4'-di-tert-butyldiphenylamine,
  iii) 2,4,4'-tris-tert-butyldiphenylamine,
δ) compounds of the group
  i) 4-tert-butyl-4'-tert-octyldiphenylamine,
  ii) o,o', m,m', or p,p'-di-tert-octyldiphenylamine,
  iii) 2,4-di-tert-butyl-4'-tert-octyldiphenylamine,
ε) compounds of the group
  i) 4,4'-di-tert-octyldiphenylamine,
  ii) 2,4-di-tert-octyl-4'-tert-butyldiphenylamine, and
wherein not more than 5% by weight of component α), 8 to 15% by weight of component β), 24 to 32% by weight of component γ), 23 to 34% by weight of component δ) and 21 to 34% by weight of component ε) are present.

TABLE 1

| example | tested sample | temperature of onset [° C.] |
|---|---|---|
| 35a)[a] | 100 parts polyol without stabilizer composition | 132 |
| | 100 parts polyol with 0.45 parts stabilizer composition containing compound | |
| 35b)[b] | (201) | 188 |
| 35c)[b] | (202) | 193 |
| 35d)[b] | (205) | 193 |
| 35e)[b] | (206) | 197 |
| 35f)[b] | (207) | 194 |
| 35g)[b] | (214) | 194 |
| 35h)[b] | (215) | 195 |
| 35i)[b] | (216) | 193 |
| 35j)[b] | (218) | 191 |
| 35k)[b] | (219) | 192 |
| 35l)[b] | (220) | 192 |
| 35m)[b] | (222) | 191 |
| 35n)[b] | (223) | 189 |
| 35o)[b] | (224) | 190 |

[a] comparative
[b] according to the invention

EXAMPLE 36

Stabilization of Polyether/Polyurethane Soft Foam

Preparation of Polyether/Polyurethane Soft Foam:
0.71 g of a stabilizer composition (0.45 parts based on 100 parts of polyol), which consists of Irganox 1135 (RTM BASF; phenolic antioxidant as described at example 35; 0.32 parts based on 100 parts of polyol), Irganox 5057 (RTM BASF; aminic antioxidant as described at example 35; 0.10 parts based on 100 parts of polyol) and a compound of formula I according to the invention (0.03 parts based on 100 parts of polyol), is dissolved in 157.1 g Lupranol 2084 (RTM BASF; polyol as described in example 35). In case of comparative examples 36a) and 36f), no stabilizer composition is added. 9.84 g of a solution consisting of 1.88 g Tegostab BF 2370 (RTM Evonik Industries; surfactant based on polysiloxane), 0.24 g Tegoamin 33 (RTM Evonik Industries; general purpose catalyst based on triethylene diamine) and 7.7 g of deionized water are added and the reaction mixture is stirred vigorously for 10 seconds at 2600 rpm. 0.31 g Kosmos 29 (RTM Evonik Industries; gelling catalyst based on stannous octoate) is then added and the reaction mixture is again stirred vigorously for 18 seconds at 2600 rpm. 92.19 g of Lupranat T80 (RTM BASF; toluene-2,4- and toluoylene-2,6-diisocyanate mixture) is then added with continuous stirring for 5 to 7 seconds at 2600 rpm. The mixture is then poured into a 20×20×20 cm cake-box and an exothermic foaming reaction takes place as indicated by an increase of temperature. The foam blocks are cooled and stored at room temperature for 24 hours.

All prepared foam blocks show a comparable initial white colour.

Anti-Scorch Testing

Scorch resistance is determined by static heat aging, i.e. static alu-block test. The foam blocks are cut into thin tubes (2 cm thick, 1.5 cm in diameter). From each foam block, a thin tube is taken as foam sample. The foam sample is heated in an aluminum block.

The temperature is kept at 180° C. for 30 minutes.

The scorch resistance is assessed by measuring the colour of the foam sample after aging. The measured colour is reported in terms of Yellowness Index (YI) determined on the foam sample in accordance with the ASTM 1926-70 Yellowness Test. Low YI values denote little discoloration and high YI values severe discoloration of the samples. The whiter a foam sample remains, the better the foam sample is stabilized.

TABLE 2

| example | employed polyol component | Yellowness index after 30 minutes at 180° C. |
|---|---|---|
| 36a)[a)] | 100 parts polyol without stabilizer composition | 26 |
| | 100 parts polyol with 0.45 parts stabilizer composition containing compound | |
| 36b)[b)] | (201) | 1 |
| 36c)[b)] | (222) | 2 |
| 36d)[b)] | (223) | 1 |
| 36e)[b)] | (224) | 3 |

Footnotes are listed at table 1.

TABLE 3

| example | employed polyol component | Yellowness index after 30 minutes at 180° C. |
|---|---|---|
| 36f)[a)] | 100 parts polyol without stabilizer composition | 25 |
| | 100 parts polyol with 0.45 parts stabilizer composition containing compound | |
| 36g)[b)] | (202) | 2 |
| 36h)[b)] | (205) | 1 |
| 36i)[b)] | (206) | 1 |
| 36j)[b)] | (207) | 1 |

TABLE 3-continued

| example | employed polyol component | Yellowness index after 30 minutes at 180° C. |
|---|---|---|
| 36k)[b)] | (214) | 2 |
| 36l)[b)] | (215) | 1 |
| 36m)[b)] | (216) | 2 |
| 36n)[b)] | (218) | 2 |
| 36o)[b)] | (219) | 2 |
| 36p)[b)] | (220) | 2 |

Footnotes are listed at table 1.

EXAMPLE 37

Stabilization of Polypropylene

Method 1:

The employed mini-extruder, which is commercially available from DSM, enables a flow of the melted polymer in a circle, i.e. two screws in a twin-screw arrangement press the melted polymer to the outlet, which is connected to the inlet zone of the extruder. The temperature of the steel barrel of the mini-extruder can be regulated and the inlet zone of the extruder can be purged with a gas, which allows the removal of entrapped air originating from the loading of the polymer sample. Furthermore, a sensor determines the force, which is exerted by the melted polymer onto the barrel during rotation of the two screws. A change in the viscosity of the melted polymer leads to a change of the force.

The steel housing of the extruder is set at a temperature of 280° C. and the inlet zone is set under a nitrogen flow of 20 mL/min. At a screw speed of 50 rpm, 9 g of a mixture, which consists of 8.955 g of a pipe grade polypropylene random copolymer (99.95% of the overall mixture) and 0.0045 g of a compound according to the invention (0.05% of the overall mixture) are loaded. In case of comparative example 37a), a compound according to the invention is not added. Said polypropylene random copolymer itself already contains 0.2% tetrakis-[3-(3,5-di-tert-butyl-4-hydroxy-phenyl)-propionyloxymethyl]-methane, 0.2% 1,3,5-tri-(2,6-tert-butyl-4-hydroxybenzyl)-2,4,6-trimethylbenzene, 0.1% tris-(2,4-di-tert-butylphenyl)phosphite and 0.05% calcium stearate.

Tetrakis-[3-(3,5-di-tert-butyl-4-hydroxy-phenyl)-propionyloxymethyl]methane is a phenolic antioxidant, which is contained for example in Irganox 1010 (RTM BASF), as depicted:

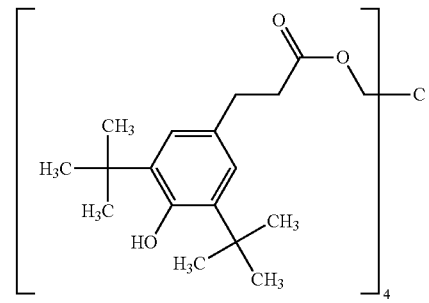

1,3,5-Tri-(2,6-tert-butyl-4-hydroxybenzyl)-2,4,6-trimethylbenzene is a phenolic antioxidant, which is contained for example in Irganox 1330 (RTM BASF), as depicted:

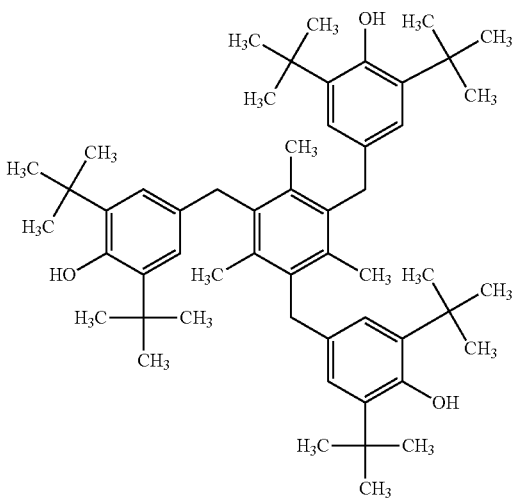 [SMILES: Cc1c(Cc2cc(C(C)(C)C)c(O)c(C(C)(C)C)c2)c(C)c(Cc2cc(C(C)(C)C)c(O)c(C(C)(C)C)c2)c(C)c1Cc1cc(C(C)(C)C)c(O)c(C(C)(C)C)c1]

Tris-(2,4-di-tert-butylphenyl)phosphite is a phosphite stabilizer, which is contained for example in Irgafos 168 (RTM BASF), as depicted:

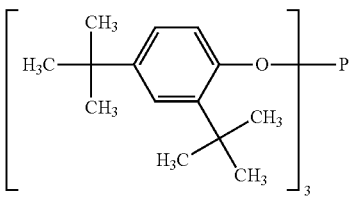

After loading, the screw speed is set to 100 rpm and the force exerted on the barrel is recorded. The test is conducted for 10 min under nitrogen at a flow rate of 20 mL/min. After a short period, a steady decrease of the force is recorded. The decrease of the force is quantified as slope of the force-to-time curve, wherein the slope is calculated between the time period of 7 and 10 minutes. The curve is rather linear during said period. The decrease of the force with time is taken as degree of melt-degradation of the polymer sample.

Desired is a minimum of degradation, which is expressed by a small value for the slope of the curve. No degradation would mean zero slope.

The results are shown in table 4.

Method 2: Multiple Pass Extrusion Test 2500 g of polypropylene random copolymer (as described under method 1 including the mentioned additives) is blended with 1.25 g of a compound according to the invention and compounded under nitrogen at 220° C. with a twin screw extruder. In case of comparative example 37t), a compound according to the invention is not added. The pellets are extruded 5 more times at 280° C. under air. The melt flow of the pellets after the 5$^{th}$ extrusion is measured at 230° C. with a weight of 5 kg according to ISO 1133:1997.

A very small change of the melt index indicates less degradation. Ideally, there would be no change in melt flow.

The results are shown in table 5.

TABLE 4

| example | tested composition | method 1 [slope] |
| --- | --- | --- |
| 37a)[a)] | without addition of a compound according to the invention | −0.8 |
| | with compound | |
| 37b)[b)] | (201) | −0.2 |
| 37c)[b)] | (202) | −0.45 |
| 37d)[b)] | (205) | −0.48 |
| 37e)[b)] | (206) | −0.54 |
| 37f)[b)] | (207) | −0.47 |
| 37g)[b)] | (209) | −0.42 |
| 37h)[b)] | (210) | −0.38 |
| 37i)[b)] | (211) | −0.4 |
| 37j)[b)] | (214) | −0.56 |
| 37k)[b)] | (216) | −0.4 |
| 37l)[b)] | (218) | −0.44 |
| 37m)[b)] | (219) | −0.43 |
| 37n)[b)] | (220) | −0.31 |
| 37o)[b)] | (221) | −0.34 |
| 37p)[b)] | (222) | −0.19 |
| 37q)[b)] | (223) | −0.14 |
| 37r)[b)] | (224) | −0.17 |
| 37s)[b)] | (226) | −0.09 |

Footnotes are listed at table 1.

TABLE 5

| example | tested composition | method 2 [melt flow (5 kg/ 230° C.) after 5th extrusion] |
| --- | --- | --- |
| 37t)[a)] | without addition of a compound according to the invention | 3.35 |
| | with compound | |
| 37u)[b)] | (201) | 2.6 |
| 37v)[b)] | (222) | 2.2 |
| 37w)[b)] | (224) | 2.6 |

Footnotes are listed at table 1.

The invention claimed is:

1. A composition, which comprises
a) a polyolefin; and
b) a compound of formula I

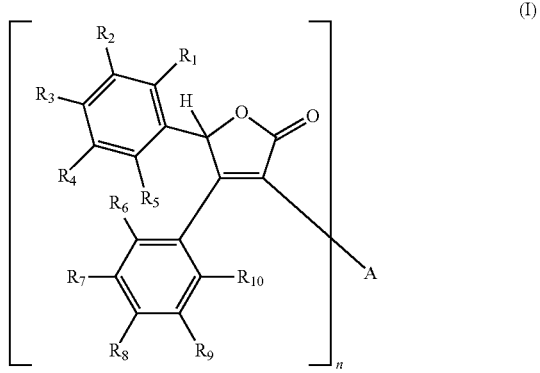

wherein
n is 1,
A is phenyl which is substituted by one or more $C_1$-$C_8$-alkyl, $C_1$-$C_4$-alkoxy, $C_5$-$C_7$-cycloalkyl or halogen; and
$R_1$, $R_2$, $R_3$, $R_4$, $R_5$, $R_6$, $R_7$, $R_8$, $R_9$ and $R_{10}$ are H.

2. A composition according to claim 1, wherein in the compound of formula I,
A is phenyl which is substituted by one to three $C_1$-$C_8$-alkyl or $C_1$-$C_4$-alkoxy.

3. A composition according to claim 1, wherein component b) is contained in an amount of 0.0005% to 10% based on the weight of component a).

4. A composition according to claim 1, which comprises c) a further additive.

5. A composition according to claim 4, which comprises c) an additive selected from the group consisting of a phosphite, a phosphonite, an acid scavenger, a phenolic antioxidant and an aminic antioxidant.

6. A composition according to claim 4, wherein the weight ratio of b) to c) is from 4:1 to 1:20.

7. A composition according to claim 5, which comprises d) a second further additive selected from the group consisting of a phosphite, a phosphonite, an acid scavenger, a phenolic antioxidant and an aminic antioxidant.

8. A process for protection of a polyolefin, which process comprises incorporating into or applying onto the organic material a compound of formula I

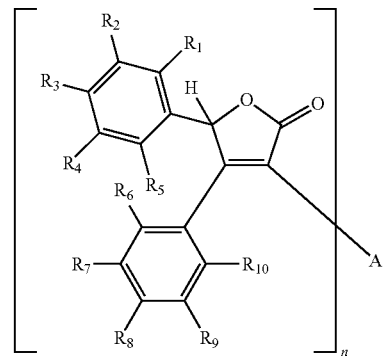

wherein
n is 1,
A is phenyl which is unsubstituted or substituted by one or more $C_1$-$C_8$-alkyl, $C_1$-$C_4$-alkoxy, $C_5$-$C_7$-cycloalkyle or halogen;
$R_1$, $R_2$, $R_3$, $R_4$, $R_5$, $R_6$, $R_7$, $R_8$, $R_9$ and $R_{10}$ are H.

* * * * *